(12) United States Patent
Kaulich et al.

(10) Patent No.: US 12,091,656 B2
(45) Date of Patent: Sep. 17, 2024

(54) METHOD FOR GENERATING HIGHER ORDER GENOME EDITING LIBRARIES

(71) Applicant: Johann Wolfgang Goethe-Universität Frankfurt am Main, Frankfurt am Main (DE)

(72) Inventors: Manuel Kaulich, Frankfurt am Main (DE); Andreas Ernst, Frankfurt am Main (DE); Martin Wegner, Bad Nauheim (DE); Valentina Diehl, Frankfurt am Main (DE); Rahel De Bruyn, Wuerzburg (DE); Svenja Wiechmann, Frankfurt am Main (DE)

(73) Assignee: Johann Wolfgang Goethe-Universität Frankfur (DE)

( * ) Notice: Subject to any disclaimer, the term of this patent is extended or adjusted under 35 U.S.C. 154(b) by 726 days.

(21) Appl. No.: 16/472,645

(22) PCT Filed: Dec. 27, 2017

(86) PCT No.: PCT/EP2017/084625
§ 371 (c)(1),
(2) Date: Jun. 21, 2019

(87) PCT Pub. No.: WO2018/122248
PCT Pub. Date: Jul. 5, 2018

(65) Prior Publication Data
US 2019/0330616 A1  Oct. 31, 2019

(30) Foreign Application Priority Data

Dec. 29, 2016  (DE) .......................... 102016125894.6

(51) Int. Cl.
| | | |
|---|---|---|
| *C12N 15/10* | (2006.01) | |
| *C07H 21/02* | (2006.01) | |
| *C07H 21/04* | (2006.01) | |
| *C40B 20/04* | (2006.01) | |
| *C40B 30/04* | (2006.01) | |
| *C40B 40/02* | (2006.01) | |
| *C40B 40/06* | (2006.01) | |

(52) U.S. Cl.
CPC .......... *C12N 15/102* (2013.01); *C07H 21/02* (2013.01); *C07H 21/04* (2013.01); *C12N 15/1037* (2013.01); *C12N 15/1072* (2013.01); *C40B 20/04* (2013.01); *C40B 30/04* (2013.01); *C40B 40/02* (2013.01); *C40B 40/06* (2013.01); *C12Y 207/07007* (2013.01); *C12Y 302/02027* (2013.01); *C12Y 605/01001* (2013.01)

(58) Field of Classification Search
CPC ....... C12N 15/102; C40B 20/04; C40B 30/04; C40B 40/02
See application file for complete search history.

(56) References Cited

U.S. PATENT DOCUMENTS

| | | | | |
|---|---|---|---|---|
| 6,156,509 A | * | 12/2000 | Schellenberger | .... C12N 15/102 435/235.1 |
| 2006/0068406 A1 | * | 3/2006 | Affholter | ............ C12N 15/1027 435/6.13 |
| 2006/0183123 A1 | * | 8/2006 | Salerno | ................... C12N 15/10 435/6.16 |
| 2014/0363850 A1 | * | 12/2014 | Salerno | ................... C12P 19/34 435/194 |
| 2015/0064138 A1 | * | 3/2015 | Lu | ......................... A61K 38/465 435/320.1 |

FOREIGN PATENT DOCUMENTS

| | | | |
|---|---|---|---|
| CN | 103911376 A | 7/2014 | |
| WO | WO-2016025131 A1 * | 2/2016 | ........... C12N 15/102 |

OTHER PUBLICATIONS

Sakuma, Tetsushi, et al. "Multiplex genome engineering in human cells using all-in-one CRISPR/Cas9 vector system." Scientific reports 4.1 (2014): 1-6. (Year: 2014).*
Koferle et al. ("CORALINA: a universal method for the generation of gRNA libraries for CRISPR-based screening." BMC genomics 17.1 (2016): 1-13 ) (Year: 2016).*
Koferle 2016 supplementary materials) (Year: 2016).*
International Search Report and Written Opinion; International Patent Application No. PCT/EP2017/084625; Apr. 25, 2018 (16 pages).
Seeger et al., "Complete Spectrum of CRISPR/Cas9-induced Mutations on HBV cccDNA", Molecular Therapy: The Journal of the American Society of Gene Therapy, vol. 24, No. 7, Jul. 1, 2016, pp. 1258-1266.
Dong et al., "Targeting hepatitis B virus cccDNA by CRISPR/Cas9 nuclease efficiently inhibits viral replication", Antiviral Research, Elsevier BV, vol. 118, Apr. 3, 2015, pp. 110-117.

(Continued)

*Primary Examiner* — Sahana S Kaup
(74) *Attorney, Agent, or Firm* — Merchant & Gould P.C.

(57) ABSTRACT

The present invention pertains to a novel method for the generation of highly diverse RNA expressing vectors and vector libraries for use in targeted gene knock out, knock down and genome modification approaches. The invention pertains to a method for generating such higher order libraries without the need of classical cloning technologies. This is particularly useful for libraries based on large vectors wherein a sequence cannot be easily mutated with classical mutagenesis methods. The vectors and libraries generated according to the methods of the invention are in particular for RNA assisted silencing technologies such as RNA interference, and for targeted genome editing using the clustered regularly interspaced short palindromic repeats (CRISPR)/Cas system or similar RNA/DNA-encoded gene perturbation systems which use small guide RNAs to target the CRISPR complex to a specific genomic sequence. The invention provides also kits comprising the materials for performing the methods of the invention.

Figure 1:
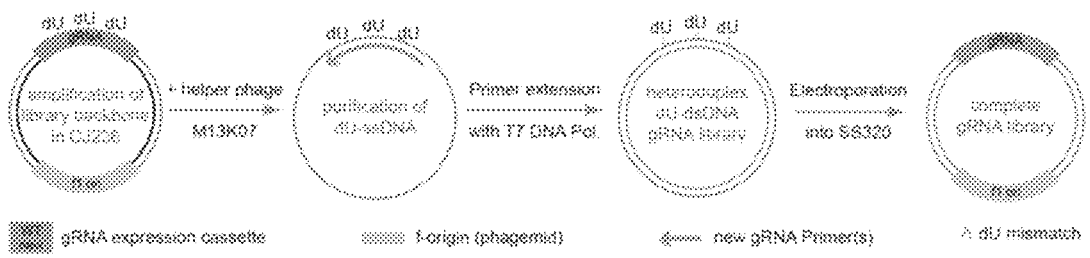
Figure 1:
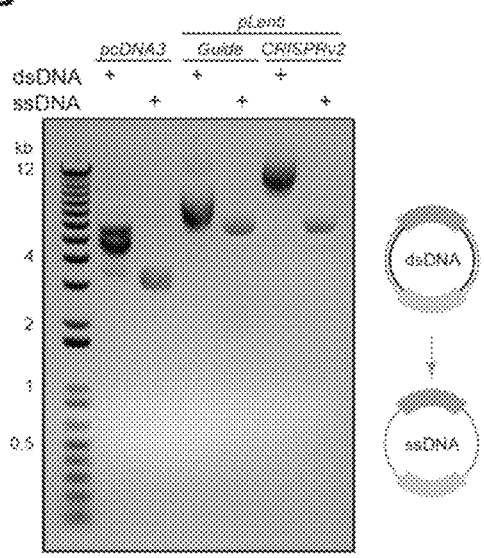
Figure 1:
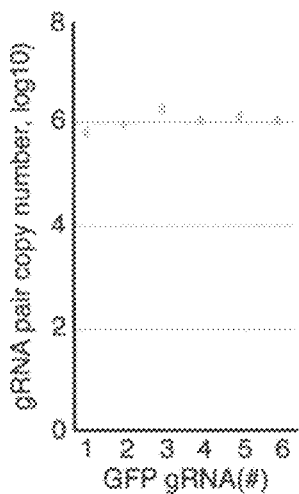
Figure 1:
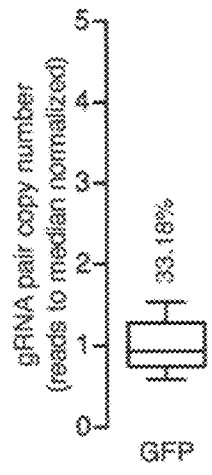

19 Claims, 8 Drawing Sheets
Specification includes a Sequence Listing.

(56) References Cited

OTHER PUBLICATIONS

Kennedy et al., "Suppression of hepatitis B virus DNA accumulation in chronically infected cells using a bacterial CRISPR/Cas RNA-guided DNA endonuclease", Virology, vol. 476, Feb. 1, 2015, pp. 196-205.
Mali et al., "Supplementary Materials for RNA-Guided Human Genome Engineering via Cas9", Science, vol. 339, No. 6121, Jan. 3, 2013, pp. 823-826.
Köferle et al., "Coralina: a universal method for the generation of gRNA libraries for CRISPR-based screening", BMC Genomics, Biomed Central Ltd, vol. 17, No. 1, Nov. 14, 2016, pp. 1-13.
Ming et al., "Progress in Protein Side-Directed Mutagenesis", Guizhou Science, vol. 17, No. 4, pp. 308-315, Dec. 1999, with English abstract.

* cited by examiner

A

B

C  D a

SEQUENCE LISTING

```
<160> NUMBER OF SEQ ID NOS: 17

<210> SEQ ID NO 1
<211> LENGTH: 20
<212> TYPE: DNA
<213> ORGANISM: artificial
<220> FEATURE:
<223> OTHER INFORMATION: primer
```

<400> SEQUENCE: 1
aaaacatcga ccgaaagcgt                                                                                           20

<210> SEQ ID NO 2
<211> LENGTH: 40
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (18)..(21)
<223> OTHER INFORMATION: n is a, c, g, or t
<220> FEATURE:
<221> NAME/KEY: misc_feature
<222> LOCATION: (23)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 2
gctctaaaac ybbndhdnnn ndnnnnnhnn cggtgtttcg                                                                      40

<210> SEQ ID NO 3
<211> LENGTH: 46
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 3
ctagctctaa aacybbndhd nnnndnnnnn hnncggtgtt tcgtcc                                                               46

<210> SEQ ID NO 4
<211> LENGTH: 50
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (23)..(26)
<223> OTHER INFORMATION: n is a, c, g, or t
<220> FEATURE:
<221> NAME/KEY: misc_feature
<222> LOCATION: (28)..(32)

<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 4
ttctagctct aaaacybbnd hdnnnndnnn nnhnncggtg tttcgtcctt            50

<210> SEQ ID NO 5
<211> LENGTH: 56
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t
<220> FEATURE:
<221> NAME/KEY: misc_feature
<222> LOCATION: (31)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 5
tatttctagc tctaaaacyb bndhdnnnnd nnnnnhnncg gtgtttcgtc ctttcc      56

<210> SEQ ID NO 6
<211> LENGTH: 50
<212> TYPE: DNA
<213> ORGANISM: artificial
<220> FEATURE:
<223> OTHER INFORMATION: primer

<400> SEQUENCE: 6
ttctagctct aaaacaggtg aagttcgagg gcgaccggtg tttcgtcctt            50

<210> SEQ ID NO 7
<211> LENGTH: 50
<212> TYPE: DNA
<213> ORGANISM: artificial
<220> FEATURE:
<223> OTHER INFORMATION: primer

<400> SEQUENCE: 7
ttctagctct aaaacccctg agcaaagacc ccaaccggtg tttcgtcctt            50

<210> SEQ ID NO 8
<211> LENGTH: 50
<212> TYPE: DNA
<213> ORGANISM: artificial
<220> FEATURE:
<223> OTHER INFORMATION: primer

<400> SEQUENCE: 8
ttctagctct aaaactcgtg accaccctga cctaccggtg tttcgtcctt            50

<210> SEQ ID NO 9
<211> LENGTH: 51
<212> TYPE: DNA
<213> ORGANISM: artificial

<220> FEATURE:
<223> OTHER INFORMATION: primer

<400> SEQUENCE: 9
ttctagctct aaaaccggcg cgggtcttgt agttgccggt gtttcgtcct t          51

<210> SEQ ID NO 10
<211> LENGTH: 50
<212> TYPE: DNA
<213> ORGANISM: artificial
<220> FEATURE:
<223> OTHER INFORMATION: primer

<400> SEQUENCE: 10
ttctagctct aaaacttcag ctcgatgcgg ttcaccggtg tttcgtcctt             50

<210> SEQ ID NO 11
<211> LENGTH: 50
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (16)..(35)
<223> OTHER INFORMATION: n is a, c, g, or t

<400> SEQUENCE: 11
ttctagctct aaaacnnnnn nnnnnnnnnn nnnnncggtg tttcgtcctt             50

<210> SEQ ID NO 12
<211> LENGTH: 50
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (23)..(26)
<223> OTHER INFORMATION: n is a, c, g, or t
<220> FEATURE:
<221> NAME/KEY: misc_feature
<222> LOCATION: (28)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 12
ttctagctct aaaacybbnd hdnnnndnnn nnhnncggtg tttcgtcctt             50

<210> SEQ ID NO 13
<211> LENGTH: 36
<212> TYPE: DNA
<213> ORGANISM: artificial
<220> FEATURE:
<223> OTHER INFORMATION: primer

<400> SEQUENCE: 13
gcgggatcct tacttgtaca gctcgtccat gccgag                           36

<210> SEQ ID NO 14
<211> LENGTH: 22
<212> TYPE: DNA

```
<213> ORGANISM: artificial
<220> FEATURE:
<223> OTHER INFORMATION: primer

<400> SEQUENCE: 14
cacatcccgc gagatccaga cg                                              22

<210> SEQ ID NO 15
<211> LENGTH: 50
<212> TYPE: DNA
<213> ORGANISM: Artificial
<220> FEATURE:
<223> OTHER INFORMATION: Primer

<400> SEQUENCE: 15
ttctagctct aaaaccggtg aacagctcct cgccccggtg tttcgtcctt                50

<210> SEQ ID NO 16
<211> LENGTH: 56
<212> TYPE: DNA
<213> ORGANISM: artificial
<220> FEATURE:
<223> OTHER INFORMATION: shRNA sequence

<400> SEQUENCE: 16
ccggtcctaa ggttaagtcg ccctcgctcg agcgagggcg acttaacctt aggttt         56

<210> SEQ ID NO 17
<211> LENGTH: 56
<212> TYPE: DNA
<213> ORGANISM: artificial
<220> FEATURE:
<223> OTHER INFORMATION: shRNA sequence

<400> SEQUENCE: 17
ccggaagcaa agaccccaac gagaactcga gttctcgttg gggtctttgc tttttt         56
```

METHOD FOR GENERATING HIGHER ORDER GENOME EDITING LIBRARIES

FIELD OF THE INVENTION

The present invention pertains to a novel method for the generation of highly diverse RNA expressing vectors and vector libraries for use in targeted gene knock out, knock down and genome modification approaches. The invention pertains to a method for generating such higher order libraries without the need of classical cloning technologies. This is particularly useful for libraries based on large vectors wherein a sequence cannot be easily mutated with classical mutagenesis methods. The vectors and libraries generated according to the methods of the invention are in particular for RNA assisted silencing technologies such as RNA interference, and for targeted genome editing using the clustered regularly interspaced short palindromic repeats (CRISPR)/Cas system or similar RNA/DNA-encoded gene perturbation systems which use small guide RNAs to target the CRISPR complex to a specific genomic sequence. The invention provides also kits comprising the materials for performing the methods of the invention.

DESCRIPTION

The clustered regularly interspaced short palindromic repeats (CRISPR)/Cas system was initially discovered in bacterial and archaeal species as a defense mechanism against foreign genetic material (e.g. plasmids and bacteriophages). The naturally occurring CRISPR/Cas systems rely on expression of three components: 1) a guide RNA sequence that is complementary to a target sequence, 2) a scaffold RNA that aids in recruiting the third component, an endonuclease, to the site. Though in many bacterial and archaeal species CRISPR/Cas systems are used to degrade foreign genetic material, the system has been adapted for use in a wide variety of prokaryotic and eukaryotic organisms and has been used for many methods including gene knockout, mutagenesis, and expression activation or repression (Hsu, et al. Cell (2014) 157(6): 1262-1278). In genetically engineered CRISPR/Cas systems, the requirement for three independent components can be circumvented by expression of a small guide RNA (sgRNA, or simply guide RNA-gRNA) that contains both the CRISPR guide RNA sequence for binding a target sequence and the scaffold RNA that together mimics the structure formed by the individual guide RNA sequence and scaffold sequence and is sufficient to recruit the endonuclease to the appropriate target site (Jinek, et al. Science (2012) 337(6096):816-821). An additional prerequisite for successful DNA targeting of the Cas-gRNA complex is the presence of a protospacer-adjacent motif (PAM) DNA sequence in the target DNA, for which the exact sequence depends on the bacterial Cas-enzyme (12-15). For the most widely used *Streptococcus pyogenes* Cas9 (SpCas9) this sequence has the format of NGG, where N can be any nucleotide. Most notably, the Cas enzyme can be expressed in human cells and, by providing a human DNA-directed gRNA, induce a highly specific DNA double strand break that cannot be repaired, leading to insertion and deletion (InDel) mutations (13, 16). Phenotypes of InDel mutations range from in-frame deletions to complete gene knockouts. Recently, the CRISPR/Cas system has been demonstrated to efficiently correct a mutation responsible for sickle cell disease by using patient-derived stem and progenitor cells (17). Hence, the CRISPR/Cas system is a programmable gene-editing tool with enormous potential, ranging from standard cell biology to therapeutic applications (18).

Single genetic changes can be used to generate well-controlled model systems, but these do not allow for unbiased screenings. To perform genetic screens, a multitude of gRNA sequences can be combined to generate libraries, targeting specific regions in the human and other genomes (19-22). Major advantages of these genetic screens are their unbiased application and ease of use. As of today, only a couple of genome-wide CRISPR/Cas knockout screens have been published, but the pace in which these experiments are performed and respective results are reported has accelerated tremendously. In addition to knockout screens, a handful of laboratories have demonstrated the benefits of genome-wide CRISPR/Cas transcriptional activation and repression screens (23-27). Areas covered by these screens include drug resistance, cellular growth, recessive and essential genes, longnon-coding RNAs (lncRNAs) as well as NF-KB activating/repressive genes, or metastasis inducing genes (28-30).

The currently available gRNA libraries differ significantly in their design and extent. The first published libraries were based on lentiCRISPRv1 and -v2 plasmids from the laboratory of Feng Zhang (McGovern, Broad, MIT, Boston, USA) and were designed on principles of genomic presence of the PAM sequence (19). More recent libraries are designed based on machine-learning algorithms that optimize gRNA activity and minimize potential off-target effects in the human (Brunello-library) and mouse (Brie-library) genome, thereby providing higher confidence in primary results (31, 32). Two basic principles distinguish these genome-wide libraries: 1) the algorithms used to predict and select functional gRNAs, and 2) the overall complexity of the libraries, which is mainly determined by the total number of gRNAs to target a single gene, ranging from 4 to 12 for Brunello and Toronto KnockOut (30, 32), respectively. Methods to generate these libraries are based predominantly on conventional restriction enzyme-digestion or Gibson Assembly-directed cloning. As such, these libraries contain an up to several hundredfold bias towards a subset of gRNAs that directly impedes the scale and quality of subsequent applications and results (19, 32). Hence, there is an urgent need for novel methods to generate RNA/DNA-encoded gene perturbation libraries of any complexity without undesired biases.

The object of the invention is solved in one aspect by a method for generating a covalently closed circularized (ccc) DNA based small RNA/DNA expression vector or vector library, the method comprising the steps of
(a) Providing a single stranded (ss) phagemid vector comprising (i) at least one small RNA/DNA expression cassette comprising a RNA/DNA promoter and an empty targetsmall-RNA/DNA-sequence-introduction-site or a small RNA/DNA coding sequence and/or a DNA/RNA nuclease target sequence, or partial sequence thereof, (ii) at least one origin for replication (ORI) of single strand DNA such as a phage ORI, and in particular a f1-origin, and
(b) Providing at least one species of mutagenic RNA or DNA-Primer, wherein the mutagenic RNA or DNA-primer has the following structure in 3' to 5' direction: a first homology region, a target sequence region encoding for a small RNA/DNA to be expressed, and a second homology region, wherein the first homology region is complementary to, or is capable of annealing to, a sequence of the ss-phagemid vector construct flanking the empty target-small-RNA/DNA-sequence-introduction-site or the small RNA/

DNA coding sequence, or partial sequence thereof, on the 5' side, and wherein the second homology region is complementary to, or is capable of annealing to, a sequence of the ss-phagemid vector construct flanking the empty target-small-RNA/DNA-sequence-introduction-site or the small RNA/DNA coding sequence, or partial sequence thereof, on the 3' side, (c) Annealing of at least one species of mutagenic RNA or DNA-primer to the ss-phagemid vector construct and amplifying a covalently closed circularized (ccc)heteroduplex dsDNA therefrom, (d) removing residual wild type phagemid vector DNA.

For removing residual wild type phagemid vector DNA endonuclease digestion may be applied. For example, an endonuclease target site is provided in the single stranded (ss) phagemid vector construct within its' at least one small RNA/DNA expression cassette. Preferably the endonuclease target site is located in the single stranded (ss) phagemid vector construct between the regions which are complementary to the first homology region of the mutagenic DNA-Primer and the region complementary to the second homology region of the mutagenic primer. Thus, the endonuclease target site is located at a position which is not duplicated in 3Cs synthesis and is therefore present only in the wild type ss-phagemid vector construct. Hence, the method comprises here within step (d), enzymatically digesting the 3Cs DNA with an endonuclease specific for the target site. For example as endonucleases in some embodiments restriction enzymes and their target sites are used. Exemplary restriction enzymes and their target sites are I-PpoI, SmaI, HpaI, I-SceI or I-CeuI. Any restriction recognition site can be used that do not occur in the template ss DNA nor in the introduced sequence I the mutagenic primer. In addition to the use of restriction endonucleases also any one of the following enzymes can be used to remove residual wild type plasmid: I-CeuI, I-PpoI, I-SceI, all homing endonucleases are preferred, all non-homing endonucleases, the usage of gene-perturbation target sequences for e.g. TALEN, ZFN, CRISPR/Cas and similar enzymes, the usage of prokaryotic and/or eukaryotic toxic nucleotide sequences with the aim of suppressing the amplification of such sequences and the usage of homology and/or recombination-based cloning sequences.

Another possibility to remove wild type DNA vector is to use the Kunkel method. Hence, the above problem is solved by the present invention by a method for the generation of a small RNA/DNA expressing (or encoding) vector, or a method of introducing a small RNA/DNA coding sequence into a vector, using the method of Kunkel for mutagenesis (Kunkel method). Preferred aspects therefore pertain to a method of introducing a small RNA/DNA sequence into a vector using the Kunkel method or Kunkel mutagenesis. The Kunkel method or Kunkel mutagenesis in context of the invention refers to the following procedure: the DNA fragment to be mutated is inserted into a phagemid (any f1 ori containing vector such as M13mp18/19) and is then transformed into an E. coli strain deficient in two enzymes, dUTPase (dut) and uracil deglycosidase (ung). Both enzymes are part of a DNA repair pathway that protects the bacterial chromosome from mutations by the spontaneous deamination of dCTP to dUTP. The dUTPase deficiency prevents the breakdown of dUTP, resulting in a high level of dUTP in the cell. The uracil deglycosidase deficiency prevents the removal of uracil from newly synthesized DNA. As the double-mutant E. coli replicates the phage DNA, its enzymatic machinery may, therefore, misincorporate dUTP instead of dTTP, resulting in single-strand DNA that contains some uracils (ssUDNA). The ssUDNA is extracted from the bacteriophage that is released into the medium, and then used as template for mutagenesis. An oligonucleotide containing the desired mutation or change in nucleotide sequence is used for primer extension. The formed heteroduplex DNA consists of one parental non-mutated strand containing dUTP and a mutated strand containing dTTP. The DNA is then transformed into an E. coli strain carrying the wildtype dut and ung genes. Here, the uracil-containing parental DNA strand is degraded, so that nearly all of the resulting DNA consists of the mutated strand. The method of the invention is in particular suitable for introducing guide RNA sequences into a genome editing vector for targeted genome editing.

A "Kunkel method" in context of the invention is a method comprising the amplification with a mutated primer using a single stranded uracilated DNA as a template, preferably a circular single stranded uracilated DNA. "Uracilated" shall refer to any DNA molecule containing one or more uracil bases in a nucleotide.

In preferred embodiments of the invention the above method is a method for generating a covalently closed circularized (ccc) DNA based small RNA/DNA expression vector or vector library, the method comprising the steps of (a) Providing a single stranded (ss) phagemid vector construct comprising at least one uracil base and/or a DNA/RNA nuclease target site; the ss-phagemid vector construct comprising (i) at least one small RNA/DNA expression cassette comprising a RNA/DNA promoter and an empty target-small-RNA/DNA-sequence-introduction-site or a small RNA/DNA coding sequence, or partial sequence thereof, (ii) at least one origin for replication (ORI) of single strand DNA such as a phage ORI, and in particular a f1-origin, and (b) Providing at least one species of mutagenic DNA-primer, wherein the mutagenic DNA-primer has the following structure in 3' to 5' direction: a first homology region, a target sequence region encoding for a small RNA/DNA to be expressed, and a second homology region, wherein the first homology region is complementary to, or is capable of annealing to, a sequence of the ss-phagemid vector construct flanking the empty target-small-RNA/DNA-sequence-introduction-site or the small RNA/DNA coding sequence, or partial sequence thereof, on the 5' side, and wherein the second homology region is complementary to, or is capable of annealing to, a sequence of the ss-phagemid vector construct flanking the empty target-small-RNA/DNA-sequence-introduction-site or the small RNA/DNA coding sequence, or partial sequence thereof, on the 3' side, (c) Annealing of at least one species of mutagenic DNA primer to the ss-phagemid vector construct and amplifying a covalently closed circularized (ccc)heteroduplex dsDNA, (d) Replacing the uracil-containing strand in the ccc-heteroduplex dsDNA with a non-uracil containing complementary DNA strand to obtain a cccDNA based small RNA/DNA expression vector or vector library.

Herein, the term "phagemid" refers to a phage genome which has been converted into a plasmid.

In one preferred embodiment, the single stranded (ss) phagemid vector construct comprises additionally within its at least one small RNA/DNA expression cassette a restriction enzyme recognition site (restriction site). Preferably the restriction site is located in the single stranded (ss) phagemid vector construct between the regions which are complementary to the first homology region of the mutagenic DNA-Primer and the region complementary to the second homology region of the mutagenic primer. Thus, the restriction site is located at a position which is not duplicated in 3Cs synthesis and is therefore present only in the uracil containing ss-phagemid vector construct. The embodiment allows the additional digest of residual uracilated wild type DNA. Hence, the method in one embodiment further comprises a step of (c') between steps (c) and (d), comprising enzymatically digesting the 3Cs DNA with a restriction enzyme capable of a selective introduction of a double strand break at the restriction site. In context of the embodiment restriction sites, and their corresponding enzymes, are used which have a recognition sites which is rarely found in genomes. Exemplary restriction enzymes and their target sites are I-PpoI, SmaI, HpaI, I-SceI or I-CeuI. Any restriction recognition site can be used that do not occur in the template uricilated ss DNA. In addition to the use of restriction endonucleases also any one of the following enzymes can be used to remove residual wild type plasmid: I-CeuI, I-PpoI, I-SceI, all homing endonucleases are preferred, all non-homing endonucleases, the usage of gene-perturbation target sequences for e.g. TALEN, ZFN, CRISPR/Cas and similar enzymes, the usage of prokaryotic and/or eukaryotic toxic nucleotide sequences with the aim of suppressing the amplification of such sequences and the usage of homology and/or recombination-based cloning sequences.

In one preferred embodiment the invention provides a single stranded (ss) phagemid vector construct as described before, comprising at least two small RNA/DNA expression cassettes, more preferably at least three, 4, 5, 6, 7, 8, 9, 10, 15, 20, 30 and more small RNA/DNA expression cassettes as described herein before. In this embodiment, referred to as "multiplex", the vector molecule is able to generate a multitude of small RNA/DNAs to be expressed simultaneously.

In one additional embodiment, the at least one small RNA/DNA expression cassette, is at least two or more small RNA/DNA expression cassettes (multiplex expression of gRNA or other small RNA/DNA). In other preferred embodiments, the restriction sites used within the two or more small RNA/DNA expression cassettes are identical, similar or different.

The term "covalently closed circularized DNA" or "cccDNA" as used herein refers to DNA molecules that have assumed a circular form in contrast to linear DNA molecules such as eukaryotic chromosomal DNA or bacterial chromosomal DNA that comprises a nick or comprises a free 3'- or 5'-end. Moreover, the circular structure of the above referenced DNA molecules is covalently closed. cccDNA is well known in the art and is further described, for example, in KG. Hardy (ed) "Plasmids, a practical approach", IRL Press Oxford U.K., Washington D.C., U.S.A., 1987.

As used herein, the term "vector library" refers to a plurality of vectors (or plasmids) comprising a plurality of unique small RNA/DNA sequences to be expressed (e.g., siRNA, shRNA, gRNA or similar sequences) inserted in a RNA/DNA expression cassette. In preferred embodiments, vector libraries comprise at least $10^1$ or $10^2$, more preferably, at least $10^3$, even more preferably at least $10^4$, and still further more preferably, at least $10^5$, $10^6$, $10^7$, $10^8$ or $10^9$ unique vector sequences (meaning RNA/DNA sequences contained in each vector or plasmid).

In context of the present invention a small RNA shall be understood to include an siRNA, shRNA, an anti-miR, a guide RNA (gRNA) or guide DNA (gDNA). Most preferred is that the small RNA is a gRNA, and wherein the ss-phagemid vector construct comprises further, but is not limited to the presence of, a genome editing nuclease expression sequence, optionally operably linked to a promoter.

The present invention in some preferred embodiments seeks to provide a new method for the generation of higher order libraries of small RNA/DNA expressing vectors. In context of the invention, the term "higher order" shall mean that the library comprises multiple species of vectors which are different in the sequence of the small RNA/DNA to be expressed by/via the vector. The present method uses the mutagenic DNA-primer to introduce such sequences into the vector of choice. Therefore, in some embodiments the at least one species of mutagenic DNA-primer is at least two species of mutagenic DNA-primer, preferably is at least three, more preferably at least 4, 5, 6, 10, 50, 100, 1000, $10^4$, $10^5$, $10^6$, $10^7$, $10^8$, $10^9$, $10^{10}$, $10^{11}$ or $10^{12}$, species of mutagenic DNA-primer, and wherein each species of cccDNA has a different sequence in the small RNA/DNA coding sequence of choice.

In some embodiments of the present invention, the multitude of mutagenic DNA-primer sequence species are provided by introducing into the small RNA/DNA coding sequence (as contained in the mutagenic DNA-primer of the invention) of choice at least one or more IUPAC-encoded bases (e.g. degenerated base). A "degenerate base" or "degenerate position" is in the sequence nomenclature referred to as an "n". In context of the present invention a degenerate base is not a type of nucleotide base, but denotes the possibility that in a preparation of nucleic acids having essentially the same sequence, the position "n" in said sequence allows the possibility of multiple kinds of bases at this position. Therefore, a preparation of nucleic acids having a sequence containing at least one "n" position denotes a mixture of nucleic acids having either adenine, guanine, thymine, or cytosine (with equal probability) at the position n. For example, if oligonucleotides are synthesized, the reaction at one or more positions may be conducted using as donor nucleotides an equal amount of adenine, guanine, thymine, and cytosine containing nucleotides. In such a reaction, each of these nucleotides have an equal chance to be added to the growing oligonucleotide chain, and therefore allows the creation of a mixture of molecules with different bases at the position "n". The same principle can be used if at one positions only two or three different bases are intended to be introduced. In the present disclosure the following nomenclature is used: R=G, A (purine), Y=T, C (pyrimidine), K=G, T (keto), M=A, C (amino), B=G, T, C (all but A), D=G, A, T (all but C), H=A, C, T (all but G), V=G, C, A (all but T) and N=A, G, C, T (any).

In other embodiments of the present invention the small RNA/DNA coding sequence is at least 10 nucleotides to 200 nucleotides long, more preferably 10 to 100, more preferably 10 to 50, more preferably 10 to 30, more preferably 15 to 30, more preferably 15 to 25, most preferably 17 to 23, most preferably about 20. The sequence length may be adjusted by the skilled artisan depending on the type of small RNA/DNA to be expressed. The preferred length of guide RNA and shRNA or siRNA are different, but are well known to the skilled artisan.

The mutagenic DNA-primer of the invention comprises flanking homology regions which are used to anneal the primer with the ss circular uracilated vector molecule used in the reaction of the invention. The flanking regions are therefore preferably of a length that allows for an annealing of the mutagenic DNA-primer to the template at conditions suitable for primer extension. The lengths of the 3' or 5' homology regions may be identical or different. In some embodiments, each of the homology regions has a length of at least 5 nucleotides, preferably at least 10 nucleotides, more preferably 5 to 40 nucleotides, most preferably 10 to 30, or 10 to 20, most preferably 13 to 18, and even more preferably about 15 nucleotides. Most preferred are 5-40 nucleotides. In some other embodiments of the invention the mutagenic DNA-primer has a sequence as shown in any of SEQ ID NO: 2 to 12.

In some embodiments of the method of the invention the single stranded (ss) phagemid vector construct is provided by the following additional method steps:
  (aa) amplification of a dsDNA phagemid vector of the same sequence in a bacterial strain deficient for dUTPase and/or uracil glycosylase, and/or their homologs, paralogs or orthologues, preferably in the CJ236 strain, to obtain uracil containing heteroduplex dsDNA phagemid vectors and
  (bb) generation of phage particles comprising an uracil containing ssDNA, and
  (cc) purifying from said phage particles said uracil containing ssDNA to obtain the ss-phagemid vector construct comprising at least one uracil base.

In another embodiment preferred according to the invention, the bacterial strain deficient for dUTPase and/or uracil glycosylase, and/or their homologs, paralogs or orthologues, preferably the CJ236 strain, comprises a helper phagemid, or wherein in step (bb) said bacterial strain deficient for dUTPase and/or uracil glycosylase, and/or their homologs, paralogs or orthologues, preferably in the CJ236 strain in infected with a helper phage, wherein the helper phagemid or helper phage is preferably M13K07.

In some embodiments it is preferred that step (d) of the method of the invention is performed by transforming and amplifying said ccc-heteroduplex dsDNA in a bacterium having a functional dUTPase and/or uracil glycosylase activity, such as XL1 or SS320, to obtain said cccDNA.

In some embodiments, the method of the invention is for the generation of vectors suitable for genome editing. Such genome editing vectors are usually characterized by the presence of a guide RNA expression cassette which comprises a site for the introduction of the gRNA sequence of choice which will guide the genome editing complex to the target site in the genome. As such the gRNA expression cassette comprises both the gRNA portion for targeting and the gRNA segment for binding to the genome editing nuclease (Cas). The gRNA expression cassette is usually in operable linkage (transcriptional control) with an RNA promoter such as the human or mouse U6 promoter or human 7SK promoter or mouse H1 promoter. However, other RNA promoters are known to the skilled artisan. The genome editing vector usually further includes an expressible genome editing nuclease such as Cas9.

As used herein, the term "guide RNA" generally refers to an RNA sequence or molecule (or a group of RNA molecules collectively) that can bind to a Cas protein and aid in targeting the Cas protein to a specific location within a target polynucleotide (e.g., a DNA or RNA). A guide RNA can comprise a crRNA segment and a tracrRNA segment. As used herein, the term "crRNA" or "crRNA segment" refers to an RNA molecule or portion thereof that includes a polynucleotide-targeting guide sequence, a stem sequence, and, optionally, a 5'-overhang sequence. As used herein, the term "tracrRNA" or "tracrRNA segment" refers to an RNA molecule or portion thereof that includes a protein-binding segment (e.g., the protein-binding segment is capable of interacting with a CRISPR-associated protein, such as a Cas9). The term "guide RNA" encompasses a single guide RNA (sgRNA), where the crRNA segment and the tracrRNA segment are located in the same RNA molecule. The term "guide RNA" also encompasses, collectively, a group of two or more RNA molecules, where the crRNA segment and the tracrRNA segment are located in separate RNA molecules.

The term "scaffold" refers to the portions of guide RNA molecules comprising sequences which are substantially identical or are highly conserved across natural biological species. Scaffolds include the tracrRNA segment and the portion of the crRNA segment other than the polynucleotide-targeting guide sequence at or near the 5' end of the crRNA segment, excluding any unnatural portions comprising sequences not conserved in native crRNAs and tracrRNAs.

The genome editing vector of the invention may encode a f1 bacteriophage origin of replication, a RNA polymerase promoter, a guide RNA scaffold for the CRISPR/Cas system, a RNA-guided nuclease, or any other suitable alternatives thereof. Preferred constructs are *lenti* virus based constructs. Standard CRISPR/Cas vectors known in the art which may be used in context of the invention, or may serve as a blueprint for the development of other genome editing vectors are the vectors known as pLentiCRISPR, pLentiCRISPRv2 or pLentiGuide.

In some embodiments of the present invention the amplification of a covalently closed circularized (ccc)-heteroduplex dsDNA in step (c) is performed by using an enzyme having DNA polymerase activity, for example a T7 DNA polymerase, optionally in conjunction with a DNA ligase, such as T4 DNA ligase or alternatives thereof, which are known to the skilled artisan.

In another aspect, the object of the invention is solved by providing a vector or vector library generated according to the method of the invention as disclosed herein. The vector library produced according to the invention is preferably characterized by comprising at least $10^6$, more preferably $10^7$, $10^8$, and most preferably $10^9$ different species of vector sequences as described herein.

Furthermore, there is provided a method of genome wide screening cellular phenotypes, the method comprising the use of a vector library produced according to a method of the invention.

The screening method of the invention may comprise the steps of introducing the vector library of the invention—in particular the genome wide library—into a population of target cells, and phenotyping the transduced cells using any assay of interest. Any cell having a phenotype of interest can in a next step be analyzed for the identity of the transduced gRNA or RNAi, in order to identify a gene or genomic region involved in the generation of the phenotype. For example, the cells may be contacted with a cell-death inducing agent, and the surviving cells are analyzed for the transduced 3Cs vector in order to identify the genetic perturbation responsible for the resistance against the cell death-inducing agent.

In another aspect of the invention there is a kit provided for performing the method as described herein above, the kit comprising
  (a) phagemid vector construct comprising
    (i) at least one guide RNA(gRNA)/guide DNA (gDNA) expression cassette comprising a gRNA/gDNA promoter, an empty gRNA/gDNA targeting sequence introduction site or a gRNA/gDNA targeting sequence, (ii) at least one phage replication origin, and
(iii) at least one expression cassette comprising a sequence coding for a genome editing nuclease under control of a promoter sequence;
(b) a DNA polymerase, optionally a DNA ligase;
(c) a preparation of bacterial cells which have a functional dUTPase and/or uracil glycosylase activity,
(d) and, optionally, instructions for the use of the kit of the invention.

The kit may in some embodiments also include at least one or more of mutagenic DNA-primer as described and defined herein above.

In some embodiments the DNA polymerase is a T7 DNA polymerase, and/or the DNA ligase is a T4 DNA ligase, or any generally known alternatives of thereof.

In other embodiments of the invention, the phagemid vector construct of the invention is a single stranded (ss)-phagemid vector construct comprising at least one uracil base.

In further embodiments, the phagemid vector is a dsDNA vector.

The kit of the invention may in some embodiments comprise a preparation, sample or culture of bacterial cells deficient for dUTPase and/or uracil glycosylase, and/or their homologs, paralogs or orthologues, preferably the CJ236 strain. Such strains are generally known in the pertinent art.

In other embodiments pertaining to the kit of the invention, the bacterial cells further comprise/contain a helper phagemid, preferably M13K07.

In other embodiments of the invention the kit according to the invention further comprises a preparation of helper phagemid, or helper phages, wherein the helper phagemid, or helper phages, are preferably M13K07 particles.

Yet another aspect of the invention pertains to a vector library produced with the methods as described herein. Another alternative or additional aspect of the invention is a vector library comprising at least $10^1$, $10^2$, more preferably, at least $10^3$, even more preferably at least $10^4$, and still further more preferably, at least $10^5$, $10^6$, $10^7$, $10^8$ or $10^9$ unique vector sequences (meaning RNA/DNA sequences contained in each vector or plasmid). Preferred embodiments of the invention therefore pertain to a vector library, comprising a plurality of unique vector sequences, wherein the vector backbone of each vector in the library is a CRISPR/Cas9 vector, or functional alternative thereof, and each unique vector sequence in the library comprises a unique gRNA expression sequence. The number of unique gRNA sequences in such a library is preferably at least $10^1$ or $10^2$, more preferably, at least $10^3$, even more preferably at least $10^4$, and still further more preferably, at least $10^5$, $10^6$, $10^7$, $10^8$ or $10^9$. More preferably the vector library has variance of unique gRNA sequences in the library that every sequence in a given genome can be targeted with genome editing, and therefore is a truly genome wide gRNA expression library. Alternative embodiments pertain to a vector library of the invention based on a siRNA (or generally RNAi) expression vector backbone.

Further, invention relates to the following preferred items:

Item 1: A method for generating a covalently closed circularized (ccc) DNA based small RNA/DNA expression vector or vector library, the method comprising the steps of
(a) Providing a single stranded (ss) phagemid vector construct comprising at least one uracil base; the ss-phagemid vector construct comprising (i) at least one small RNA/DNA expression cassette comprising a RNA/DNA promoter and an empty target-small-RNA/DNA-sequence-introduction-site or a small RNA/DNA coding sequence and/or a DNA/RNA nuclease target sequence, or partial sequence thereof,
(ii) at least one origin for replication (ORI) of single strand DNA such as a phage ORI, and in particular a f1-origin, and
(b) Providing at least one species of mutagenic DNA-Primer, wherein the mutagenic DNA-primer has the following structure in 3' to 5' direction: a first homology region, a target sequence region encoding for a small RNA/DNA to be expressed, and a second homology region, wherein the first homology region is complementary to, or is capable of annealing to, a sequence of the ss-phagemid vector construct flanking the empty target-small-RNA/DNA-sequence-introduction-site or the small RNA/DNA coding sequence, or partial sequence thereof, on the 5' side, and wherein the second homology region is complementary to, or is capable of annealing to, a sequence of the ss-phagemid vector construct flanking the empty target-small-RNA/DNA-sequence-introduction-site or the small RNA/DNA coding sequence, or partial sequence thereof, on the 3' side,
(c) Annealing of at least one species of mutagenic DNA-primer to the ss-phagemid vector construct and amplifying a covalently closed circularized (ccc)-heteroduplex dsDNA therefrom,
(d) Replacing the uracil-containing strand in the ccc-heteroduplex dsDNA with a non-uracil containing complementary DNA strand to obtain a cccDNA based small RNA/DNA expression vector or vector library.

Item 2. The method according to item 1, wherein the small RNA is a siRNA, shRNA, an anti-miR, a guide RNA (gRNA) or guide DNA (gDNA) or any other RNA/DNA-encoded gene-perturbation sequence.

Item 3. The method according to item 2, wherein the small RNA is a gRNA, and wherein the ss-phagemid vector construct comprises further a genome editing nuclease expression sequence, optionally operably linked to a promoter (stable or inducible).

Item 4. The method according to any of items 1 to 3, wherein the at least one species of mutagenic DNA-primer is at least two species of mutagenic DNA-primer, preferably is at least three, more preferably at least 4, 5, 6, 10, 50, 100, 1000, $10^4$, $10^5$, $10^6$, $10^7$, $10^8$, $10^9$, $10^{10}$, $10^{11}$, or $10^{12}$, species of mutagenic DNA-primer, and wherein each species of cccDNA has a different sequence in the small RNA coding sequence of choice.

Item 5. The method according to any of items 1 to 4, wherein a multitude of mutagenic DNA-primer species are provided by introducing into the small RNA coding sequence of choice at least one or more degenerated bases (N).

Item 6. The method according to any one of items 1 to 5, wherein small RNA coding sequence is at least 10 nucleotides to 100 nucleotides long, more preferably 10 to 50, more preferably 10 to 30, more preferably 15 to 30, more preferably 15 to 25, most preferably 17 to 23, most preferably about 20.

Item 7. The method according to any of items 1 to 6, wherein each of the homology regions has a length of at least 5 nucleotides, preferably at least 10 nucleotides, more preferably 5 to 40 nucleotides, most preferably 10 to 30, or 10 to 20, most preferably 13 to 18, and even more preferably about 15 nucleotides.

Item 8. The method according to any of the preceding items, wherein the mutagenic DNA-primer has a sequence according to any of SEQ ID NO: 1 to 12.

Item 9. The method according to any of the preceding items, wherein the single stranded (ss)-phagemid vector construct is provided by (aa) amplification of a dsDNA phagemid vector of the same sequence in a bacterial strain deficient for dUTPase and/or uracil glycosylase, and/or their homologs, paralogs or orthologs, preferably in the CJ236 strain, to obtain uracil containing heteroduplex dsDNA phagemid vectors and (bb) generation of phage particles comprising a uracil containing ssDNA, and (cc) purifying from said phage particles said uracil containing ssDNA to obtain the ss-phagemid vector construct comprising at least one uracil base.

Item 10. The method according to item 7, wherein the bacterial strain deficient for dUTPase and/or uracil glycosylase, and/or their homologs, paralogs or orthologs, preferably in the CJ236 strain, comprises a helper phagemid, or wherein in step (bb) said bacterial strain deficient for dUTPase and/or uracil glycosylase, and/or their homologs, paralogs or orthologues, preferably in the CJ236 strain in infected with a helper phage, wherein the helper phagemid or helper phage is preferably M1307.

Item 11. The method according to any of the preceding items, wherein step (d) is performed by transforming and amplifying said ccc-heteroduplex dsDNA in a bacterium having a functional dUTPase and/or uracil glycosylase activity, such as XL1 or SS320, to obtain said cccDNA.

Item 12. The method according to any of the preceding items, wherein the amplification of a covalently closed circularized (ccc)-heteroduplex dsDNA in step (c) is performed by using an enzyme having DNA polymerase activity, for example a T7 DNA polymerase, optionally in conjunction with a DNA ligase, such as T4 DNA ligase.

Item 13. A kit for performing the method according to any of the preceding items, the kit comprising (a) phagemid vector construct comprising
　(i) at least one guide RNA(gRNA)/guide DNA (gDNA) expression cassette comprising a gRNA/gDNA promoter, an empty gRNA/gDNA targeting sequence introduction site or a gRNA/gDNA targeting sequence,
　(ii) at least one phage replication origin, and
　(iii) at least one expression cassette comprising a sequence coding for a genome editing nuclease under control of a promoter sequence;

(b) a DNA polymerase, optionally a DNA ligase;

(c) a preparation of bacterial cells which have a functional dUTPase and/or uracil glycosylase activity, (d) and instructions for use.

Item 14. A vector library obtainable by a method according to any one of items 1 to 12.

Item 15. A vector library comprising at least $10^7$, preferably at least $10^9$ unique vector sequences, wherein the vector backbone of each unique vector sequence in the library is a genome editing vector, such as a vector comprising an expressible CRISPR/Cas9 enzyme and a gRNA expression cassette.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Basic principle of covalently closed circularized synthesized (3Cs) dU-dsDNA generation. A) Graphic illustrating the essential steps of 3Cs-gRNA synthesis. B) Conventional CRISPR/Cas plasmids can be converted to dU-ssDNA, resolved by gel electrophoresis; C) Next-Generation-Sequencing (NGS) of eGFP-targeting 3Cs-gRNA library reveals the absence of sequence bias from 3Cs reactions/reagents. D) Statistical analysis of NGS (eGFP-targeting 3Cs-gRNA library) data identifies the coefficient of variation to be 33.18%, confirming the absence of sequence bias.

Figure 2:
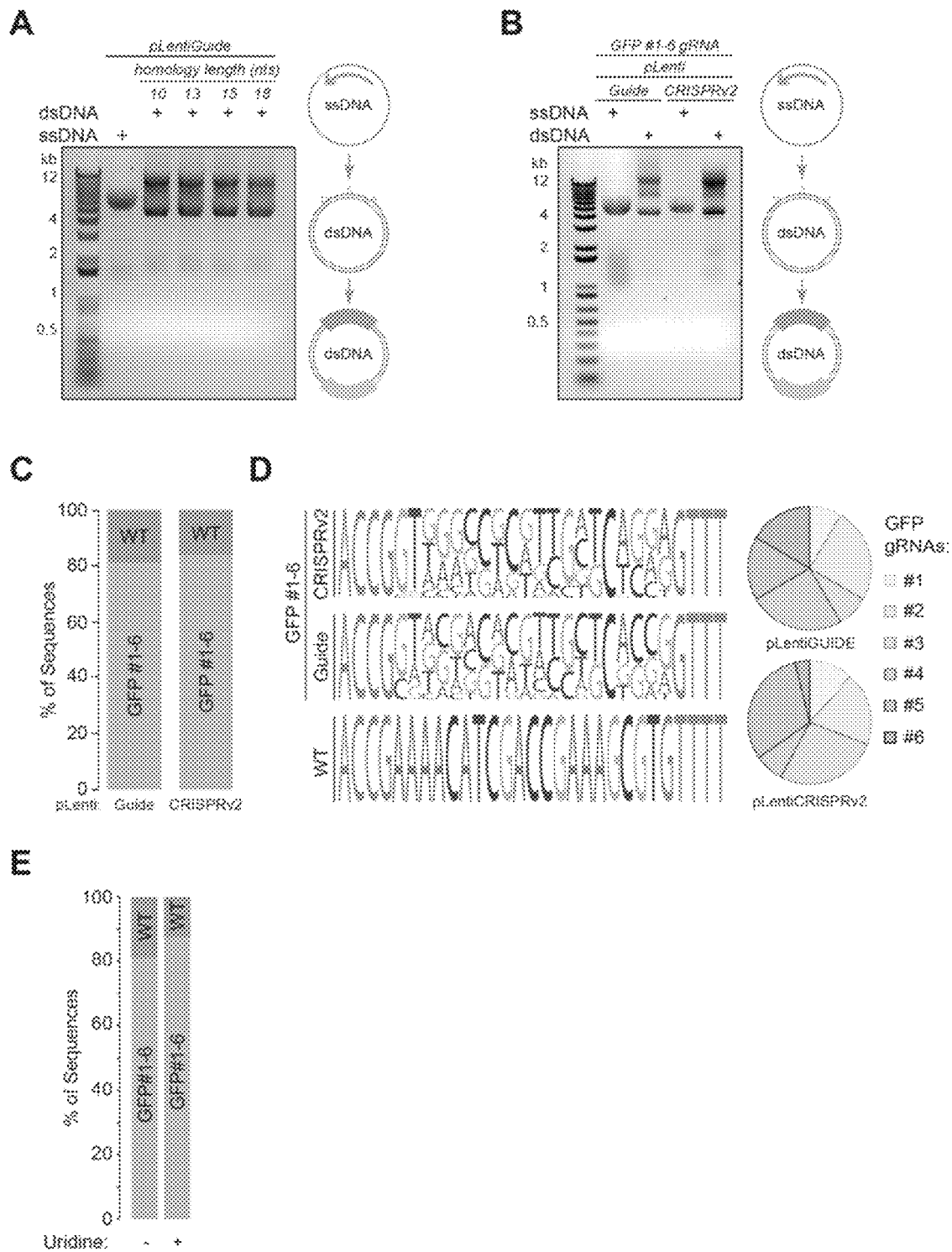

FIG. 2: Generation of eGFP-targeting 3Cs-gRNAs. A) Determining optimal 3Cs-primer homology to generate dU-3Cs-dsDNA. B) 3Cs reaction with 6 eGFP-targeting gRNA sequences. C) Ratio of mutated to wild-type sequences after amplification and clonal sequencing. D) Sequence logo of mutated gRNAs and gRNA distribution. E) Ratio of mutated to wild-type sequences when analyzed without and with additional uridine in CJ236 culture media.

Figure 3:
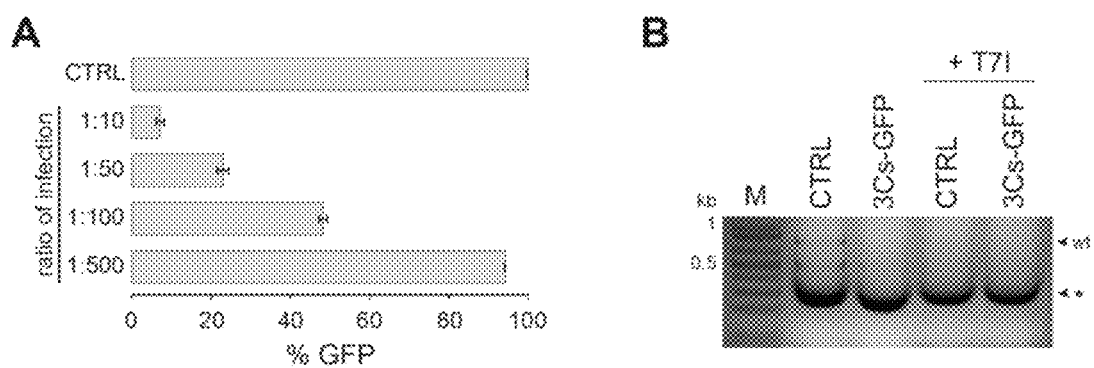

FIG. 3: 3Cs-gRNAs are functional in cells. A) Lentiviral dose-dependent reduction in green fluorescent signal after cellular transduction with eGFP-targeting 3Cs-gRNAs. B) T7 endonuclease I surveyor assay demonstrates genomic DNA editing of stable eGFP locus (wt: wild type eGFP locus, *: non-specific PCR product).

Figure 4:
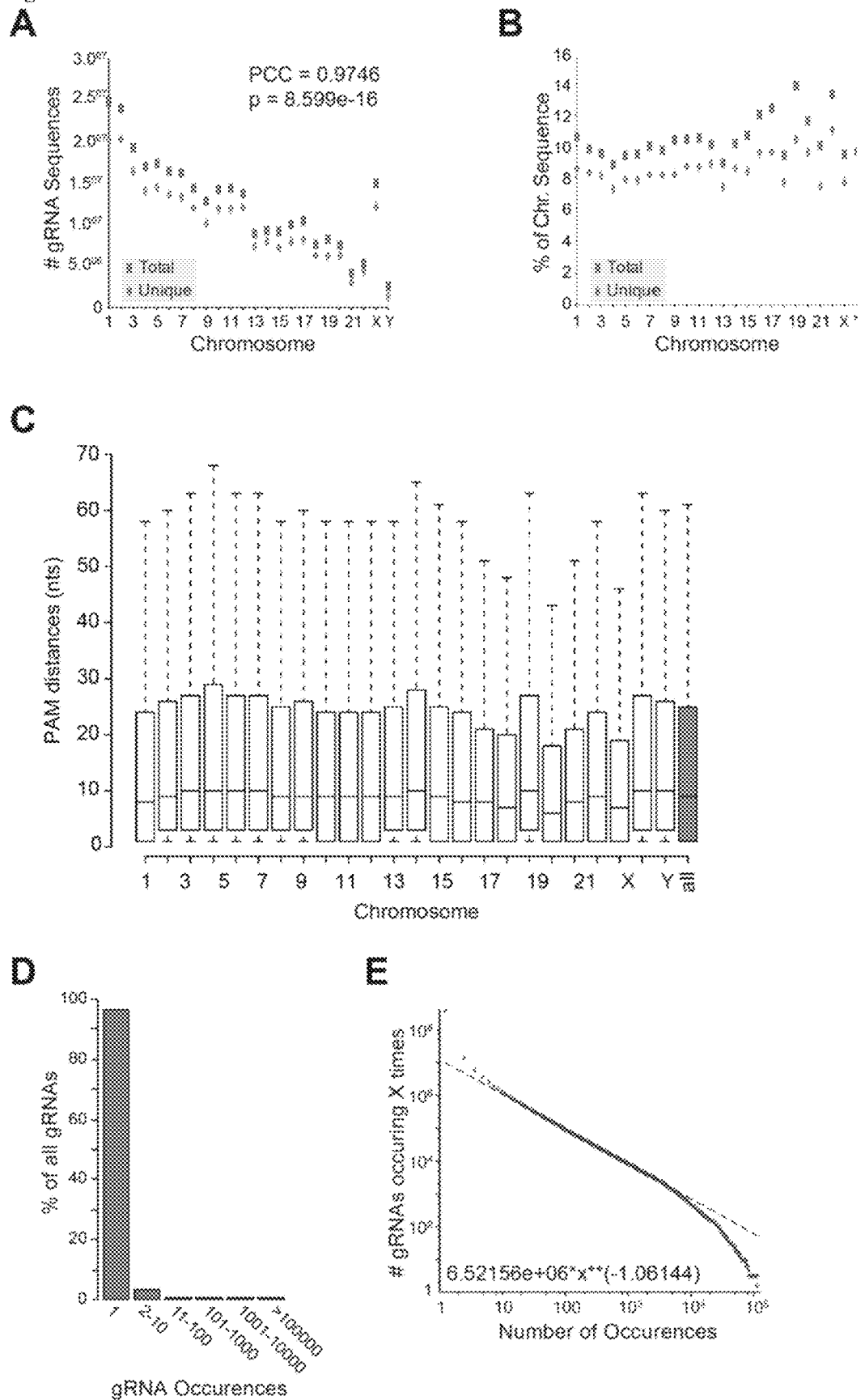

FIG. 4: Distribution of human SpCas9 targeting sites. A-B) Total and unique number of SpCas9 gRNA sequences per human chromosome. C) Average chromosomal SpCas9 PAM sequence distance in nucleotides (nts). D) Binned gRNA occurrences as percentage of all human gRNAs. E) Pareto distribution of gRNA occurrences and gRNAs occurring x times in human genome.

Figure 5:
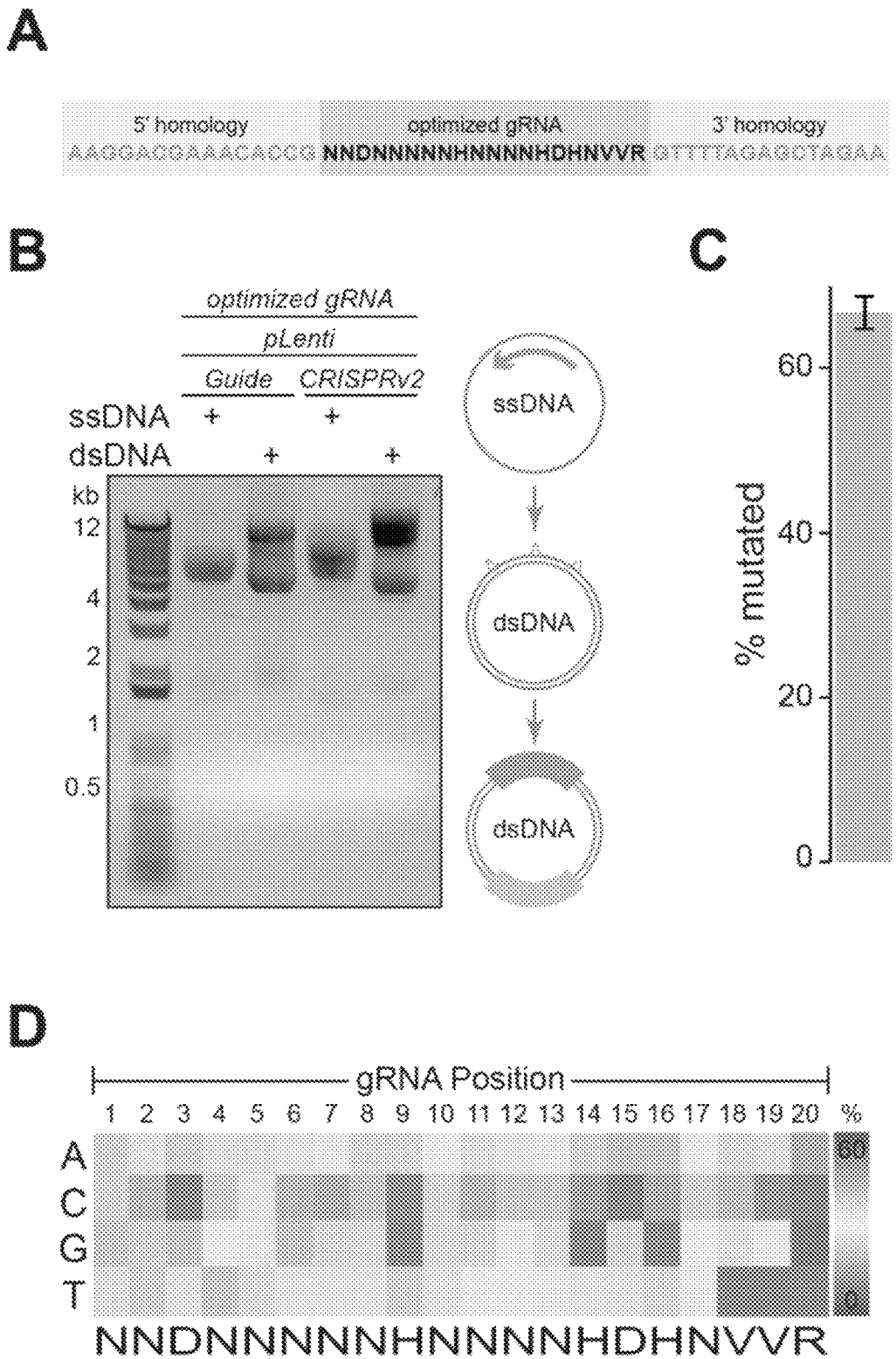

FIG. 5: A truly genome-wide 3Cs-gRNA library of optimized SpCas9 gRNAs. A) Scheme illustrating the denatured 3Cs-gRNA-primer design for optimized, highly active gRNAs. B) 3Cs reaction with optimized, denatured 3Cs primer resolved by gel electrophoresis. C) Ratio of mutated to wild-type sequences after amplification and clonal sequencing. D) 3Cs-gRNA library-sequencing, results illustrated in heat map format. The percentage of individual nucleotides per gRNA position is color-coded.

Figure 6:
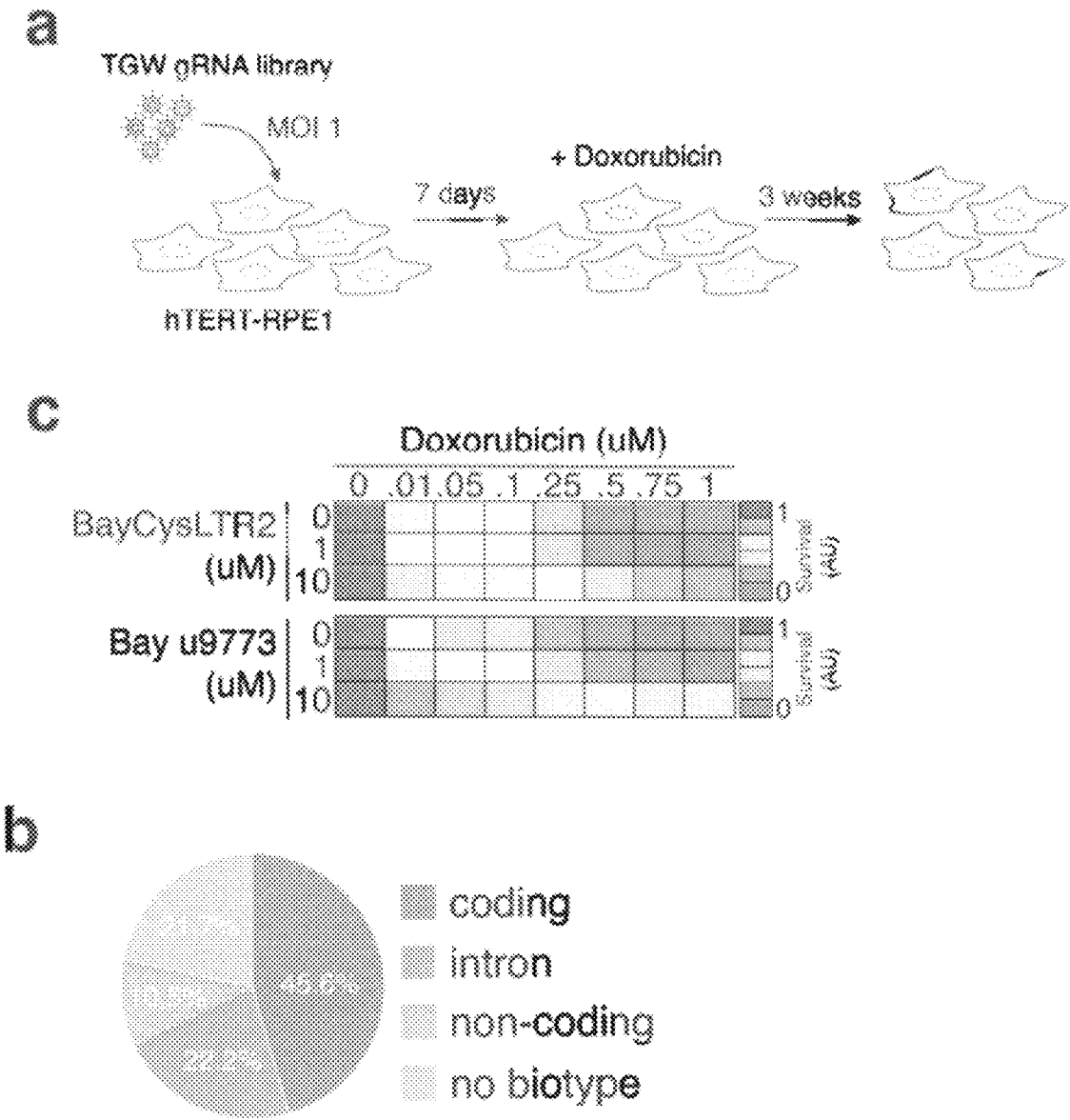

FIG. 6: Identifying Doxorubicin resistance with an optimized 3Cs-gRNA library. A) Experimental scheme illustrating the usage of hTERT-RPE1 cells, transduced with lentiviral particles (MOI=1) and selected with 1 µM Doxorubicin for three weeks. B) NGS- and bioinformatically-based identification of Doxorubicin-resistance inducing gRNAs and their location within annotated human genomic DNA. C) The CYSLTR2 gene is a reproducible protein-coding hit for which two chemical inhibitors are commercially available. Both inhibitors are titrated versus increasing concentrations of Doxorubicin and induce resistance to Doxorubicin.

Figure 7:
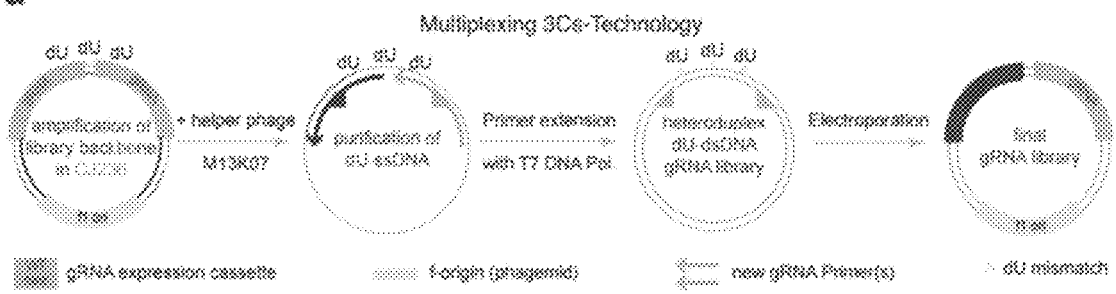
Figure 7:
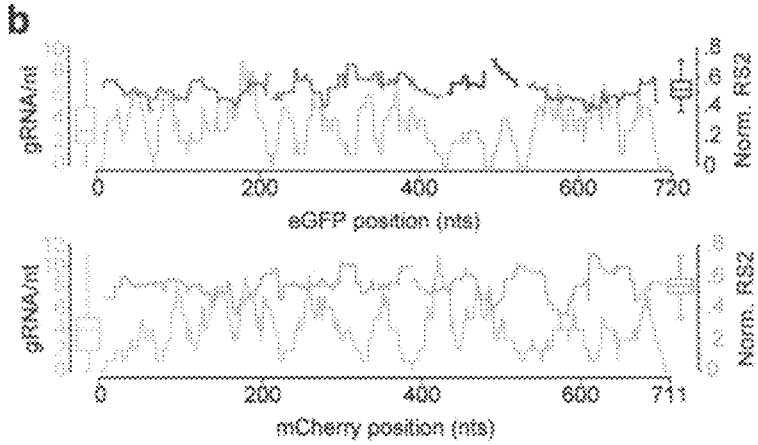
Figure 7:
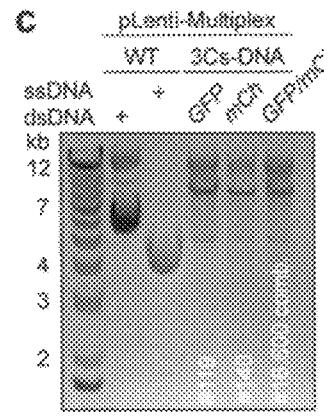
Figure 7:
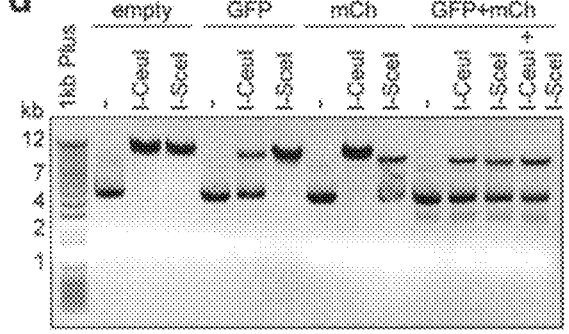
Figure 7:
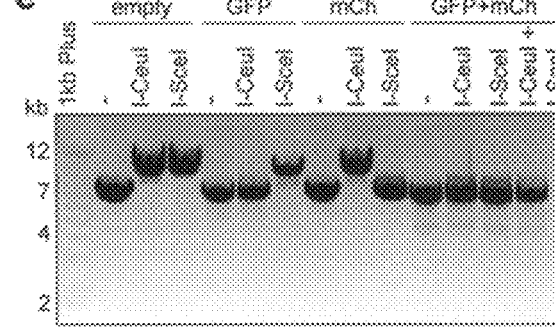
Figure 7:
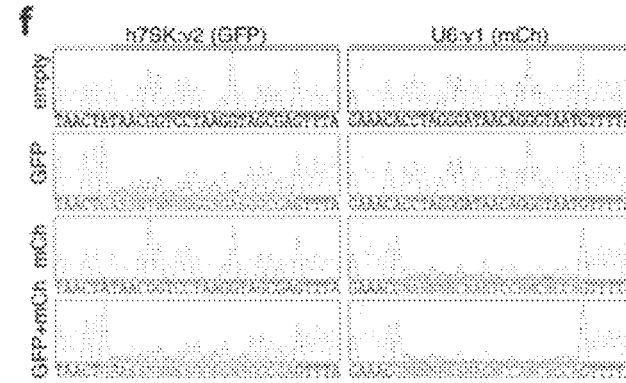
Figure 7:
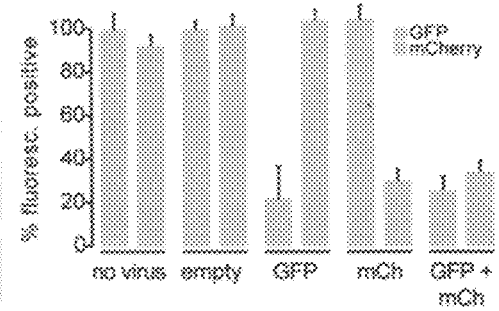

FIG. 7: General principle of generating multiplexed gRNA-containing CovalentlyClosed-Circularized synthesized (3Cs) dU-dsDNA reagents. A) Graphic illustrating the essential steps of generating multiplexed 3Cs-gRNA reagents. B) Location, quality and quantity of eGFP and mCherry genes targeting gRNAs used for the generation of multiplexed 3Cs-gRNA reagents. C) Typical 3-band pattern of successful 3Cs-reactions, resolved by gel electrophoresis (generation of eGFP, mCherry and eGFP+mCherry-targeting 3Cs-gRNA libraries). D) Quality control of first DNA purification after electroporation of 3Cs syntheses products. Purified DNA is enzymatically digested with I-CeuI, I-SceI, or combinations of both to identify reminiscents of wild-type (no gRNA inside, enzyme cleavage site inside) plasmids. Enzymatically digested DNA is then electroporated to remove wildtype reminiscents. E) Quality control of second DNA amplification reveals the absence of wild-type reminiscents. F) SANGER-sequencing of multiplexed 3Cs-gRNA libraries identifies the selective integration of gRNA sequences dependent on provided 5' and 3' homology during 3Cs reactions. G) Multiplexed 3Cs-gRNA reagents are fully functional in human cells as demonstrated by the depletion of GFP and/or mCherry depending on which lentiviral 3Cs-gRNA library is transduced into GFP/mCherry-positive cells.

Figure 8:
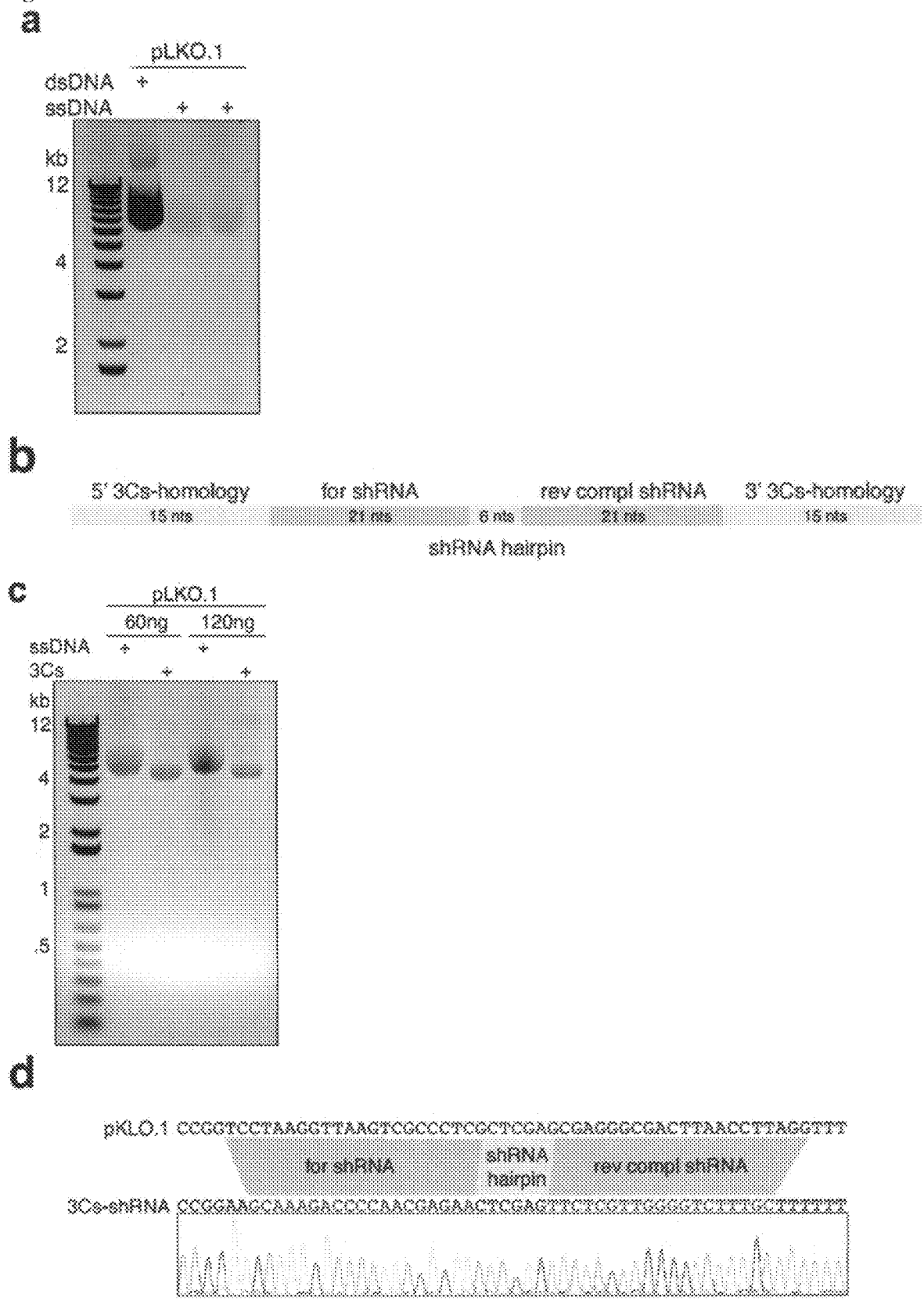

FIG. 8: 3Cs is highly versatile and enables the generation of shRNA-encoded reagents. A) Conventional lentiviral shRNA-encoding plasmids (pLKO.1) can be efficiently converted into single stranded plasmid DNA (as depicted in FIGS. 1 and 4), resolved by gel electrophoresis. B) 3Cs-shRNA primer design principle is shown. C) Typical 3-band pattern of successful 3Cs-reactions, resolved by gel electrophoresis (generation of eGFP-targeting 3Cs-shRNA). D) SANGER-sequencing of bacterial colonies derived from 3Cs-shRNA generate plasmids confirms the successful integration of eGFP-targeting shRNA sequences (highlighted in red).

EXAMPLES

Example 1: Covalently Closed Circularized Synthesized Mutated CRISPR/Cas9 Plasmids While conventional site-directed mutagenesis does not work efficiently on large retroviral elements-containing plasmids, it was anticipated that T7 DNA polymerase and T4 DNA ligase-mediated 5' oligonucleotide extension on the basis of ssDNA would be an efficient approach to generate high quality and unbiased gRNA-libraries (FIG. 1A). To this end, dut–/ung–, F-factor containing, K12 Escherichia coli CJ236 bacteria were transformed with the most widely used f1-origin (f1-ori)-containing CRISPR/Cas plasmids pLenti-Guide and pLentiCRISPRv2. In contrast to conventional K12 E. coli strains, CJ236 bacteria tolerate the presence of deoxyuridine in genomic and plasmid DNA due to the lack of the enzymes dUTPase (dut-) and uracil glycosylase (ung-). Subsequent super infection of transformed CJ236 with M13K07 bacteriophage allows the production of bacteriophage particles that package a deoxyuridine containing ssDNA (dU-ssDNA) template of pLentiGuide and pLentiCRISPRv2. In a next step, the dU-ssDNA is purified from the precipitated bacteriophage particles (FIG. 1B). In general, this approach can be applied to any plasmid that encodes an f1-ori.

To successfully generate heteroduplexed, covalently closed circularized synthesized dsDNA (3Cs-dsDNA) from dU-ssDNA templates, the optimal primer/homology length by comparing 10, 13, 15, and 18 nucleotides (nts) of 5' and 3' homology in a 2 hr in vitro 3Cs reaction was tested (FIG. 2A). The dU-CCC-dsDNA reaction products were resolved by gel-electrophoresis and the typical three-band pattern of heteroduplex dsDNA reactions was identified (33, 34). The optimal ratio between correctly extended, nicked and strand-displaced 3Cs products was achieved with 15 nts of primer homology (FIG. 2A), hence, the inventors used this length for all subsequent reactions.

Next, the inventors tested this protocol for the generation of in cell active gRNAs that target the enhanced green fluorescent protein (eGFP) gene. Six gRNA sequences were designed using the rule set 2 (RS2) algorithm and cloned using a 3Cs reaction into pLentiGuide and pLentiCRISPRv2 containing a non-human targeting (NHT) control sequence under the control of the U6 promoter and followed by the gRNA scaffold DNA sequence responsible for binding to SpCas9 (FIG. 2B) (32). The resulting heteroduplex dU-CCC-dsDNA was used to transform XL1 bacteria to determine the ratio of correctly mutated to wild type (NHT) containing sequences. The inventors individually sequenced 20 clones and determined that 81% of pLentiGuide and 82% of plentiCRISPRv2 were modified with eGFP targeting gRNAs (FIG. 2C,D). Addition of uridine to the M13K07 culture media significantly reduced the wild type rate to about 12% indicating that the occurrence of unmodified plasmid is most likely due to insufficient incorporation of dU into the dU-ssDNA template (FIG. 2E). Importantly, the inventors were able to identify several copies of all 6 eGFP-targeting gRNA sequences (FIG. 2D), even though the inventors sequenced only 20 individual clones suggesting that our highly efficient protocol is suitable for library constructions.

To test in cell functionality of our eGFP-targeting gRNA constructs, infectious lentiviral particles were generated and used to transduce eGFP-positive human telomeraseimmortalized retina pigmented epithelial (RPE1) cells. After 7 days without any selective pressure, the presence of eGFP-positive and negative cells was analyzed by flow-cytometry. The reduction of green fluorescence using the lentiviral 3Cs-gRNA constructs was very potent, while the control plasmid had no effect on eGFP fluorescence (FIG. 3A). Interestingly, the inventors observed a dose-dependent fluorescence reduction, indicating that lentiviral transduction of RPE1 cells is equally efficient as with conventionally generated lentiviral CRISPR/Cas particles (FIG. 3A). The dose-dependent reduction in green fluorescence was a direct result of genomic DNA editing by 3Cs-gRNA constructs, demonstrated by T7 surveyor assay (FIG. 3B). Hence, covalently closed circularized synthesized CRISPR/Cas gRNAs can be rapidly generated using our newly established 3C approach and are fully functional in cells.

In order to further reduce residual uracilated wild-type plasmids, the inventors modified pLentiGuide and plentiCRISPRv2 by inserting a homing enzyme restriction site for I-SceI in the gRNA cassette and repeated the 3Cs-synthesis with the eGFP targeting oligonucleotides. The presence of an I-SceI cut site facilitates the digestion and removal of unmodified wild-type plasmid after the 3Cs-reaction and reduced the occurrence of wild-type plasmid to below our SANGER-sequencing detection limit. Next generation sequencing (NGS) of the eGFP 3Cs-gRNA library (pLentiCRISPRv2 backbone) revealed a wild-type rate of below 1% and an equal presence of all 6 gRNAs with no apparent sequence bias (coefficient of variation (CV) is 33.18%) (FIGS. 1 c and d).

Example 2: Generating Highly Complex 3Cs-gRNA Libraries

Most human genome-wide SpCas9 gRNA libraries target the coding genome, which only represents approximately 1.5% of the total human genomic sequence. Hence, it was hypothesized that the method of the invention could be used to generate gRNA libraries of arbitrary complexity, but also siRNA or other small nucleic acid libraries, including a truly genome-wide scale that is not limited to the coding regions. To this end, the inventors identified in a first step all putative human SpCas9 target sites and analyzed their distribution across the individual chromosomes. The analysis demonstrates that chromosome size and PAM occurrence strongly correlate, suggesting a random distribution of SpCas9 target sites (FIG. 4A,B) with an apparent median distance of 9 nucleotides (FIG. 4C). This result is consistent with the observation that the average PAM distance in a random nucleotide sequence is approximately 8 nucleotides. The inventors identified a total of 248,985,973 ($2.5 \times 10^8$) independent gRNA sequences, of which 98% are unique in the human genome (FIG. 4D). The number of occurrence and the number of gRNAs that occur n-times in the human genome follow a direct Pareto distribution or power law (FIG. 4E), demonstrating that the vast majority of all human SpCas9 target sites are indeed unique and can be targeted with high on-target activity by established CRISPR/Cas techniques.

SpCas9 target site preferences have been previously mapped and show a clear preference for 3' puridine bases while thymidine nucleotides are disfavored (31, 32). The inventors translated the SpCas9 nucleotide preferences into an optimized 20 nts long oligonucleotide sequence that was generated by single oligonucleotide synthesis following IUPAC naming standards (FIG. 5A). In theory, this single gRNA sequence can generate a highly functional SpCas9 gRNA library that targets all possible coding and non-coding regions in the human genome. Using our established design principles for gRNAs targeting eGFP, the inventors performed the in vitro synthesis of this truly genome wide gRNA library (FIG. 5B,2B). SS320 bacteria were electroporated with the in vitro synthesis product and library diversity was determined based on the total number of transformed bacteria. In two independent reactions, an average library diversity of $1.92 \times 10^9$ was achieved resulting in a combined library of $3.8 \times 10^9$ unique gRNAs. Consequently, the newly constructed gRNA library is by 4 orders of magnitude larger than all currently available libraries. Sequencing of 200 individual clones confirmed that the mutational distribution corresponds to the nucleotide bias introduced during the synthesis of the degenerate oligonucleotide (FIG. 5C, D). Thus, the invention generated the first truly genome wide CRISPR/Cas gRNA library with a diversity of 3.8 billion unique gRNA sequences outsizing all current library designs that are currently in use. Consequently, this truly genome wide library can be used in screening approaches to dissect the functions of coding as well as non-coding regions of the human genome.

The invention presents a novel method to efficiently generate gene perturbation libraries that can be used to create libraries of any scale and diversity. Today's genome wide libraries vary in their individual complexity but span a range of $7.6 \times 10^4$ to $1.8 \times 10^5$ for Brunello and Activity-Optimized CRISPR Knockout Library (29, 32), respectively. However, even though these libraries are of high quality, they contain a bias of several ten to hundred folds for selected gRNAs, caused mainly by conventional gRNA cloning and PCR amplification of synthesized gRNA sequences. The innovative approach of the present invention uses T7 DNA polymerase in conjunction with T4 DNA ligase to mediate a 5' extension of oligonucleotides annealed on ssDNA templates of conventional CRISPR/Cas plasmids limited only by the total number of different oligonucleotides used in the 3Cs reaction. Hence, drawbacks of conventional cloning strategies are avoided.

The method of the invention can accomplish synthesis scales from few sequences to sets of highly diverse sequences. Therefore, the invention establishes a method that is applicable in different experimental settings as, e.g., generation of single-KO cell lines, intermediate sized libraries, and unbiased genome-wide libraries. Additionally, for diversities of up to several hundred sequences, the inventive method generates arrayed and pooled formats simultaneously; expanding the experimental designs to even arrayed image-based screens. Most importantly, the method of the invention generates gene perturbation libraries without seQuence Bias. Therefore, Reducing the Overall Experimental Scale and Costs Significantly.

Example 4: Screening Doxorubicin Related Genes Using the 3Cs Library

To demonstrate in cell functionality, the inventors transduced RPE1 cells with the truly genome-wide (TGW) library to identify coding and non-coding resistance mechanisms to the first-in-line chemotherapeutic agent Doxorubicin. In unperturbed conditions, Doxorubicin induces a robust and dose-dependent reduction of RPE1 cell viability within 4 days. To avoid drug escaping cells and to increase the rate of true positive findings, 1 µM of Doxorubicin was selected as the screening concentration. In a total of three biological replicates, the inventors generated lentiviral supernatant with an averaged titer of $10^7$ infectious particles per mL and screened about 600 million RPE1 cells, transduced with an MOI of 1. After an initial 7 days of selecting for lentiviral transduction, cells were exposed to 1 µM Doxorubicin and cultivated for an additional 21 days before the remaining cells were collected, their genomic DNA extracted and processed for NGS-mediated identification of gRNAs (FIG. 6a). Interestingly, among all biological replicates a significant gRNA and target overlap was identified. This suggests that it is not necessary to experimentally investigate every TGW library-containing gRNA in order to identify the majority of biological relevant hits.

From cells that survived the Doxorubicin selection, the inventors identified TGW 3Cs-gRNAs that displayed high reproducibility among biological replicates. Interestingly, while the TGW library has a strong bias towards targeting the non-coding genome, gRNAs enriched after Doxorubicin selection display an almost inverted bias towards the protein-coding genome. Of all remaining gRNAs, 45.6% are located in coding regions, 22.2% are in introns and 10.5% are in non-coding (RNA coding) regions (FIG. 6b). However, 21.7% of gRNAs are located in genomic regions for which no biotype could be assigned, indicating a gap of knowledge for those regions (FIG. 6b). To validate some of the findings in a CRISPR/Cas independent manner, the protein-coding hit gene CYSLTR2 was chosen for which two chemical antagonists are commercially available. The inventors titrated increasing concentrations of Doxorubicin against increasing concentrations of the two compounds (BayCysLTR2 and Bay u9773) and incubated drug exposed RPE1 cells for 4 days after which they were subject to the cell viability assays AlamarBlue. Interestingly, both compounds were able to revert the cytotoxic effect of Doxorubicin in a dose-dependent manner, though Bay u9773 displayed a reproducibly stronger effect (FIG. 6c). This confirms that the truly genome-wide CRISPR/Cas 3Cs-gRNA library of the invention is functional in identifying genomic regions associated with Doxorubicin resistance, and suggest that it can be applied to other biological questions as well.

Example 5: Multiplex 3Cs Libraries

Having established a protocol to generate single 3Cs-gRNA reagents, it was reasoned that the 3Cs method of the invention can efficiently perform on plasmids coding for two or more gRNAs as long as sufficient unique homology between the individual primer binding sites (cassettes) can be generated (FIG. 7a). To this end, the inventors bioinformatically identified and computed the RS2 score for all possible SpCas9 target sites in the eGFP and mCherry gene (FIG. 7b). In total 119 eGFP targeting gRNAs were identified and the inventors added 5' and 3' homology to the human S7K promoter and the second-generation SpCas9 gRNA scaffold, respectively. Oligonucleotides encoding the 140 gRNAs targeting the mCherry gene were complemented with 5' and 3' homology to the human U6 promoter and to the original SpCas9 gRNA scaffold, respectively. In three individual 3Cs reactions on the basis of a lentiviral SpCas9 gRNA multiplex plasmid (pLenti-Multiplex), the inventors generated three libraries targeting GFP, mCherry or a combination of GFP and mCherry (16.600 gRNA combinations) (FIG. 7c). The average electroporation efficiency for all independent 3Cs reactions was above $1.7*10^9$, ensuring full amplification of single and multiplexed libraries. Similar to the I-SceI clean-up step for single 3CsgRNA reagents, the inventors performed a I-CeuI (GFP cassette), I-SceI (mCherry cassette), or a combined I-CeuI/I-SceI clean-up to remove template reminiscent from the final libraries (FIG. 7d, e). The inventors SANGER-sequenced 10 bacterial plasmid colonies from each experimental condition and identified the respective gRNA region to be highly mutated, while 5' and 3' adjacent located nucleotides were free of mutational load (FIG. 7f). To functionally validate the GFP/mCherry multiplexed 3Cs-gRNA reagents, infectious lentiviral particles were induced and these were used to transduce a GFP/mCherry-positive RPE1 reporter cell line. Genomic DNA editing translated into a robust negative effect on the protein level of GFP and mCherry when analyzed by FACS analysis (FIG. 7g). Hence, the very first one-step protocol to generate multiplexed SpCas9 3Cs-gRNA libraries is presented, where the libraries are free of cloning artefacts and potentially are only limited by the number of different gRNA encoding primer sequences. Additionally, the protocol of the invention can potentially be combined with any Cas/gRNA system for gRNA multiplexing purposes expanding multiplexing reagents to the combination of different Cas-enzymes.

Example 6: Generation of 3Cs shRNA Libraries

It was demonstrated that the present 3Cs technology is very well suited to generate single and multiplexed CRISPR/Cas gene perturbation reagents of high quality. Hence, the versatility of the 3Cs technology was further tested with respect to classical RNA interference (RNAi) reagents. To test this, the inventors used the most conventional lentiviral shRNA delivery plasmid pLKO.1, from which most lentiviral CRISPR/Cas plasmids are derived, and generated ssDNA of two bacterial CJ236 clones and superinfected them with M13K07 bacteriophages, followed by phage precipitation and ssDNA purification and resolved the ssDNA by gel-electrophoresis (FIG. 8a, lane 2 and 3). The inventors then designed a 3Cs-shRNA primer, containing 15 nucleotides of 5' 3Cs-homology to the U6 RNA promoter, followed by 21 nucleotides coding for an eGFP-targeting sense shRNA, followed by the 6-nucleotide shRNA hairpin sequence, followed by 21 reverse complement nucleotides to the sense shRNA, and a 15 nucleotide 3' 3Cs-homology (FIG. 8b). The inventors applied the 3Cs-shRNA primer to two 3Cs-reaction scales (60 and 120 ng of ssDNA) and separated the 3Cs-products by gelelectrophoresis and observed the typical three-band pattern, most pronounced in the 120 ng ssDNA reaction (FIG. 8c). Bacterial transformation, plasmid DNA purification coupled to SANGER sequencing of the 120 ng 3Cs-product revealed the integration of the eGFP-targeting shRNA sequence into the pKLO.1 plasmid (FIG. 8d). This demonstrates that our 3Cs technology is not limited to the generation of CRISPR/Cas gRNA reagents, but is very versatile and can also be used to generate 3Cs-shRNA reagents for RNAi purposes.

Materials and Methods dU-ssDNA template amplification in CJ236 cells

KCM competent and dut–/ung– E. coli cells (strain K12 CJ236) were transformed with 500 ng of template plasmid, 2 µl SxKCM, and 7 µl H$_2$O and plated on LB agar supplemented with ampicillin. The next morning, colonies were picked, each into a fresh culture of 1 ml 2YT medium containing 100 µg ampicillin, 35 µg chloramphenicol, and 1:1,000 helper phage M13K07 (1e11 pfu). After 2 hours of incubation at 37° C. and 200 rpm, 25 µg kanamycin were added and shaking was continued for another 10 hours. After 10 hours, each culture was transferred to 30 ml 2YT growing medium containing 3,000 µg ampicillin, 750 kanamycin, and 187.5 µg uridine. The growing medium was incubated for 20 h at 37° C. and 200 rpm.

Purification of dU-ssDNA

After 20 h, cultures were centrifuged for 10 min at 10,000 rpm and 4° C. in a Beckman JA-12 fixed angle rotor. The phage-containing supernatant was gently mixed in a fresh falcon tube with 6 ml (1:5) PEG/NaCl (20% polyethylene glycol 8000, 2.5 M NaCl) and incubated for 30 min at room temperature to precipitate the phages. The mixture was then centrifuged for 10 min at 10,000 rpm and 4° C. The supernatant was discarded, and the phage pellet was briefly centrifuged at 4,000 rpm to remove remaining supernatant. The remaining supernatant was aspirated and phage pellets were resuspended in 1 ml PBS. The resuspended phage pellet was then centrifuged 5 min at 13,000 rpm to remove remaining cell debris. The supernatant was transferred to a fresh 1.5 ml reaction tube.

Single-stranded DNA was purified from the supernatant using the E.Z.N.A. M13 DNA Mini Kit (Omega) according to the manufactures protocol. DNA concentrations were determined using NanoDrop, and the DNA was analyzed by electrophoresing 500 ng of single-stranded DNA on a 0.8% TAE/agarose gel.

Covalently Closed Circularized Synthesized gRNAs (3Cs-gRNAs): Small and Large Scale Four constructs with primers of increasing length were synthesized in individual experiments to test for synthesis efficiency of different homology lengths using the protocol for small-scale synthesis (see "Small scale synthesis of the eGFP pool and different homology lengths"). 6 eGFP-KO constructs were synthesized in a pooled fashion using the same protocol.

The 20N and the optimized primer constructs were synthesized using a protocol for large-scale synthesis (see "Large scale synthesis of the 20N and the Opti primer"). The template plasmids that were used for both approaches, small and large-scale synthesis, were the pLentiCRISPRv2 and the pLentiGuide, each with a non human-targeting (NHT) gRNA incorporated.

The inventors used the following NHT gRNA sequence:
NHT: 5'-aaaacatcgaccgaaagcgt-3' (SEQ ID NO: 1)

To test different homology arm lengths, the inventors used the plentiGuide-NHT plasmid and the following oligonucleotides (all in 5'-3'):

10 nts:
(SEQ ID NO: 2)
gctctaaaac YBBNDHDNNNNDNNNNNHNN cGGTGTTTCG

-continued 13 nts:
(SEQ ID NO: 3)
Ctagctctaaaac YBBNDHDNNNNDNNNNNHNN cGGTGTTTCGTCC 15 nts:
(SEQ ID NO: 4)
TTCtagctctaaaac YBBNDHDNNNNDNNNNNHNN cGGTGTTTCGTCC
TT 18 nts:
(SEQ ID NO: 5)
taTTTCtagctctaaaacYBBNDHDNNNNDNNNNNHNN cGGTGTTTCGT
CCTTTCC For the pool of 6 eGFP constructs, the inventors used the pLentiGuide-NHT and the pLentiCRISPRv2-NHT, each with a pool of the following oligonucleotides (all in 5'-3'):

eGFP-1:
(SEQ ID NO: 6)
TTCtagctctaaaac aggtgaagttcgagggcgac cGGTGTTTCGTCC
TT eGFP-2:
(SEQ ID NO: 7)
TTCtagctctaaaac ccctgagcaaagaccccaac cGGTGTTTCGTCC
TT eGFP-3:
(SEQ ID NO: 8)
TTCtagctctaaaac tcgtgaccaccctgacctac cGGTGTTTCGTCC
TT eGFP-4:
(SEQ ID NO: 9)
TTCtagctctaaaac cggcgcgggtcttgtagttgC cGGTGTTTCGTC
CTT eGFP-5:
(SEQ ID NO: 10)
TTCtagctctaaaac ttcagctcgatgcggttcac cGGTGTTTCGTCC
TT eGFP-6:
TTCtagctctaaaac cggtgaacagctcctcgccc cGGTGTTTCGTCC
TT To synthesize the 20N primer (20N) and the optimized primer (Opti) the inventors used the pLentiGuide and the pLentiCRISPRv2, resulting in four conditions: 20N on pLentiGuide-NHT, 20N on pLentiCRISPRv2-NHT, Opti on pLentiGuide-NHT, and Opti on pLentiCRISPR-NHT. The 20N primer was a fully randomized primer, i.e., each nucleotide appears with equal probability at each position. The Opti primer was modeled after a previously published pattern (31, 32). In this primer, several positions were subject to constraints regarding the choice of nucleotides to scale down the size of the resulting library (all in 5'-3').

20N:
(SEQ ID NO: 11)
TTCtagctctaaaac NNNNNNNNNNNNNNNNNNNN cGGTGTTTCGTCC
TT

Opti:
(SEQ ID NO: 12)
TTCtagctctaaaac YBBNDHDNNNNDNNNNNHNN cGGTGTTTCGTCC
TT

Uridine supplementation of the growing medium

To test the effect of uridine supplementation on synthesis efficiency the inventors performed the small-scale synthesis of a pool of 6 eGFP-KO constructs with two different growing media. In one experiment, the inventors supplemented the 30 ml growing medium with 187.5 µg (6.25 µg/ml) uridine. The other experiment was performed without uridine supplementation. Apart from that, the experiments were performed according to the small-scale synthesis protocol. The synthesis products were heat shock transformed into competent $E.$ $coli$ cells, plated on LB-agar/ampicillin plates, and incubated overnight at 37° C. The ratios of wild type plasmid-containing clones versus eGFP-KO gRNA-containing clones in both experiments were determined by sequencing. 10 clones from each experiment were picked and analyzed by Sanger sequencing.

Small Scale 3Cs-gRNA Synthesis: Oligonucleotide Phosphorylation with T4 Polynucleotide Kinase To 5'-phosphorylate the oligonucleotides, the inventors combined 0.6 µg of the mutagenic oligonucleotide, 2 µl 10×TM buffer, 2 µl 10 mM ATP, 1 µl 100 mM DTT, and 20 units of T4 polynucleotide kinase. $H_2O$ was added to a total volume of 20 µl. The mixtures were incubated for 1 h at 37° C. and used immediately for annealing. For the pool of eGFP-KO constructs the inventors used 100 ng of each primer in a single reaction. The constructs with different homology lengths were synthesized individually.

Small Scale 3Cs-gRNA Synthesis: Annealing of Oligonucleotide to Template

To anneal the phosphorylated oligonucleotides to the dU-ssDNA template the inventors added 2.5 µl 10×TM buffer and 2 µl of the phosphorylated oligonucleotides to 2 µg of dU-ssDNA template and added $H_2O$ to a final volume of 25 µl. The mixture was incubated for 3 min at 90° C., 3 min at 50° C., and 5 min at 20° C. in a thermocycler.

Small Scale 3Cs-gRNA Synthesis: Enzymatic Synthesis of 3Cs-gRNAs

3Cs-dsDNA was synthesized by adding 1 µl 10 mM ATP, 1 µl 10 mM dNTP mix, 1.5 µl 100 mM DTT, 200 ligation units or 3 Weiss units T4 DNA ligase, and 3 units T7 DNA polymerase to the annealed oligonucleotide/template mixture. The synthesis mix was incubated for 2 h at room temperature. 8 µl of the reaction products were analyzed on a 0.8% TAE/agarose gel (100V, 5 min). 2 ml of the reaction products were heat shock transformed into competent $E.$ $coli$.

Small Scale 3Cs-gRNA Synthesis: Sequencing

Transformed $E.$ $coli$ were plated on LB-agar supplemented with ampicillin. The different homology arm length constructs were analyzed on a TAE/agarose gel. 20 clones of the bacteria transformed with the pool of eGFP constructs were randomly picked and analyzed by sanger sequencing to determine the distribution of gRNA sequences in the population.

Large Scale 3Cs-gRNA Synthesis: Oligonucleotide Phosphorylation with T4 Polynucleotide Kinase To 5'-phosphorylate the oligonucleotides, the inventors combined 0.6 µg of the mutagenic oligonucleotide, 2 µl 10×TM buffer, 2 µl 10 mM ATP, 1 µl 100 mM DTT, and 20 units of T4 polynucleotide kinase. $H_2O$ was added to a total volume of 20 µl. The mixtures were incubated for 1 h at 37° C. and used immediately for annealing. The 20N and the Opti primers were applied in separate synthesis reactions.

Large Scale 3Cs-gRNA Synthesis: Annealing of Oligonucleotide to Template

To anneal the phosphorylated oligonucleotides to the dU-ssDNA template the inventors added 25 µl 10×TM buffer and 20 µl of the phosphorylated oligonucleotide to 20 µg of dU-ssDNA template and added H₂O to a final volume of 250 µl. The mixture was incubated for 3 min at 90° C., 3 min at 50° C., and 5 min at 20° C. in a thermocycler.

Large Scale 3Cs-gRNA Synthesis: Enzymatic Synthesis of 3Cs-gRNAs

3Cs-ssDNA was synthesized by adding 10 µl 10 mM ATP, 10 µl 10 mM dNTP mix, 15 µl 100 mM DTT, 2000 ligation units (or 30 Weiss units) T4 DNA ligase, and 30 units T7 DNA polymerase to the annealed oligonucleotide/template mixture. The synthesis mix was incubated for 2 h at room temperature. After 2 h, the mix was affinity purified and desalted using a Qiagen QIAquick Gel Extraction Kit. To the mixture, 1 ml buffer QG (Qiagen) was added and mixed. The sample was applied to two QIAquick spin columns placed in 2 ml microcentrifuge tubes and centrifuged at 2,500 rpm for 3 min. Two spin columns were used because the binding capacity of a single column was too low for the total amount of DNA in the synthesis mix. To each column, 750 µl buffer PE (Qiagen) were added and centrifuged at 13,000 rpm for 1 min. The column was then transferred to a fresh 1.5 ml microcentrifuge tube and centrifuged at 13,000 rpm for 5 min with an open lid. The column was transferred to a fresh 1.5 ml micocentrifuge tube, 20 µl of distilled water were applied to the membrane. After 5 min, another 20 µl of distilled water were added to the column and incubated for 5 min. To elute the DNA, the columns were centrifuged at 13,000 rpm for 1 min. Eluents from the two tubes were combined in a fresh 1.5 ml microcentrifuge tube and centrifuged for 15 min at 13,000 rpm with an open lid to reduce the total volume to approximately 70 µl. 1 µl of the eluted reaction product were electrophoresed alongside the single-stranded DNA template on an 0.8% TAE/agarose gel (100V, 30 min).

Large scale 3Cs-gRNA synthesis: Electroporation

The 20N—, and optimized guide-libraries were electroporated into electrocompetent *E. coli* (strain SS320) with a Bio-Rad Gene Pulser using the following settings: resistance 200 Ohm, capacity 25, voltage 1.2 kV. To transform 100 µl of cells, 400 ng DNA were used. The electroporated cells were rescued in 4 ml of pre-warmed SOC medium and incubated for 1 h at 37° C. and 200 rpm.

After 1 h of incubation a dilution series was performed to determine the transformation efficiency and the number of transformed bacteria. 10 µl of culture were diluted 10-1 to 10-12, plated on LB agar plates with ampicillin, and incubated overnight at 37° C. The next day the electroporation efficiency and the number of transformed bacteria were determined. Remaining culture was added to 200 ml LB-medium supplemented with ampicillin and incubated overnight at 37° C. DNA was purified the next day using a Qiagen Plasmid Maxi Kit.

Large scale 3Cs-gRNA synthesis: 96-well sequencing

XL1 Blue cells were transformed via heat-shock with the purified DNA of the 20N- and the optimized guide-libraries and incubated over night at 37° C. Colonies of transformed cells were each inoculated into 450 µl 2YT medium supplemented with 100 µg/ml ampicillin and 1:1,000 M13K07 helper phage (1e11 pfu) in a 96-well plate and grown overnight at 37° C. at 200 rpm. The next day the cells were centrifuged at 4,000 rpm for 5 min. The phage-containing supernatant was diluted in a fresh 96-well plate 1:15 with PBT buffer. On a fresh 96-well plate, 2 µl of diluted phage were added to the following PCR mix: 16.9 µl distilled water, 5 µl of 5×OneTaq standard reaction buffer (NEB), 0.5 µl 10 mM dNTPs, 0.5 units of OneTaq DNA polymerase (NEB), and 0.25 µl of each 10 µM primer. The DNA fragment was amplified with the following PCR program: 5 min at 95° C., 30 cycles of amplification (30 s at 95° C., 30 s at 55° C., 40 s at 72° C.), 7 min at 72° C., and storage at 4° C. Representative reactions were analyzed on a TAE/agarose gel.

Into each well of a fresh 96-well plate, 20.8 µl of clean up mix, containing 20 µl distilled H20, 4 units of Exonuclease I, and 0.4 units of shrimp alkaline phosphatase were dispensed. 6 µl of the PCR product were transferred to each well and mixed. The clean-up reactions were incubated at 37° C. for 15 min and 80° C. for 15 min. The plate was sent for sequencing and the distribution of different gRNAs was determined.

Lentiviral Transduction

RPE1-H2B-eGFP cells were seeded in triplicates on a 6-well plate with a density of 10,000 cells per well in DMEM-F12 medium supplemented with 0.02 µg/ml Hygromycin, 110 units/ml Penicillin, 100 µg/ml Streptomycin, and 100 µl/ml FBS. Lentiviral transduction was performed the next day with increasing amounts of lentivirus harboring the pool of 6 eGFP-KO gRNAs. One well was transduced with 400 uL of a non-human target gRNA and served as a negative control. Medium was changed every second day over the course of one week. On the seventh day after transduction the degree of eGFP depletion was determined by flow cytometry.

T7 Endonuclease I surveyor assay

RPE1-H2B-eGFP cells were seeded with a density of 10.000 cells per well in DMEM/F12 medium supplemented with 0.02 µg/mL Hygromycin, 110 units/mL Penicillin, 100 µg/ml Streptomycin, and 100 µL/mL FBS. Lentiviral transduction of one well was performed the next day with 200 µL of lentiviral supernatant harboring a pool of 6 gRNAs against eGFP. Another well was transduced with a non-human target gRNA and served as a negative control. The third day after transduction the medium was changed to fresh DMEM/F12 supplemented with 0.02 µg/mL Hygromycin, 110 units/mL Penicillin, 100 µg/mL Streptomycin, and 100 µL/mL FBS. On the seventh day after transduction the genomic DNA was extracted using phenol-chloroform extraction. PCR amplification was performed with the genomic DNA samples in 50 µL reaction volume, containing 1 µg DNA, 10 µL OneTaq standard buffer, 1 µL 10 mM dNTPs, 0.25 µl OneTaq DNA polymerase, 2.5 µL the following 10 µM primers:

```
                                    (SEQ ID NO: 13)
GCGGGATCCTTACTTGTACAGCTCGTCCATGCCGAG (SEQ ID NO: 14)
CACATCCCGCGAGATCCAGACG,
``` and distilled H20 up to 50 µL of reaction volume. The following cycling conditions were used: initial denaturation for 2 min at 95° C., 30 cycles of 15 sec denaturation at 95° C., 15 sec annealing at 60° C., and 30 sec min extension at 72° C. Final extension was performed 1 min at 72° C. The two PCR amplified samples were then denatured using the following protocol: initial denaturation for 5 min at 95° C., annealing with the following ramp: 85° C. for 10 sec, 75° C. for 10 sec, 50° C. for 10 sec, and 25° C. for 1 min. 504 of the PCR products were digested with 2.7 µL of T7 Endonuclease I, and 5.5 µL NEBuffer 2 in a total volume of 58.2 µL. The mixtures were incubated for 1 h at 37° C. and analyzed on a 2.5% TAE/agarose gel.

REFERENCES

1. R. Barrangou et al., CRISPR provides acquired resistance against viruses in prokaryotes. Science 315, 1709-1712 (2007).
2. J. E. Garneau et al., The CRISPR/Cas bacterial immune system cleaves bacteriophage and plasmid DNA. Nature 468, 67-71 (2010).
3. G. Gasiunas, R. Barrangou, P. Horvath, V. Siksnys, Cas9-crRNA ribonucleoprotein complex mediates specific DNA cleavage for adaptive immunity in bacteria. Proc Natl Acad Sci USA 109, E2579-2586 (2012).
4. M. Jinek et al., A programmable dual-RNA-guided DNA endonuclease in adaptive bacterial immunity. Science 337, 816-821 (2012).
5. J. A. Doudna, E. Charpentier, Genome editing. The new frontier of genome engineering with CRISPR-Cas9. Science 346, 1258096 (2014).
6. R. Jansen, J. D. Embden, W. Gaastra, L. M. Schouls, Identification of genes that are associated with DNA repeats in prokaryotes. Molecular microbiology 43, 1565-1575 (2002).
7. A. Bolotin, B. Quinquis, A. Sorokin, S. D. Ehrlich, Clustered regularly interspaced short palindrome repeats (CRISPRs) have spacers of extrachromosomal origin. Microbiology 151, 2551-2561 (2005).
8. F. J. Mojica, C. Diez-Villasenor, J. Garcia-Martinez, E. Soria, Intervening sequences of regularly spaced prokaryotic repeats derive from foreign genetic elements. Journal of molecular evolution 60, 174-182 (2005).
9. C. Pourcel, G. Salvignol, G. Vergnaud, CRISPR elements in *Yersinia pestis* acquire new repeats by preferential uptake of bacteriophage DNA, and provide additional tools for evolutionary studies. Microbiology 151, 653-663 (2005).
10. D. H. Haft, J. Selengut, E. F. Mongodin, K. E. Nelson, A guild of 45 CRISPR-associated (Cas) protein families and multiple CRISPR/Cas subtypes exist in prokaryotic genomes. PLoS computational biology 1, e60 (2005).
11. E. Deltcheva et al., CRISPR RNA maturation by trans-encoded small RNA and host factor RNase III. Nature 471, 602-607 (2011).
12. F. A. Ran et al., Genome engineering using the CRISPR-Cas9 system. Nature protocols 8, 2281-2308 (2013).
13. P. Mali et al., RNA-guided human genome engineering via Cas9. Science 339, 823-826 (2013).
14. T. Gaj, C. A. Gersbach, C. F. Barbas, 3rd, ZFN, TALEN, and CRISPR/Cas-based methods for genome engineering. Trends Biotechnol 31, 397-405 (2013).
15. S. W. Cho, S. Kim, J. M. Kim, J. S. Kim, Targeted genome engineering in human cells with the Cas9 RNA-guided endonuclease. Nat Biotechnol 31, 230-232 (2013).
16. L. Cong et al., Multiplex genome engineering using CRISPR/Cas systems. Science 339, 819-823 (2013).
17. D. P. Dever et al., CRISPR/Cas9 beta-globin gene targeting in human haematopoietic stem cells. Nature, (2016).
18. P. *Mali*, K. M. Esvelt, G. M. Church, Cas9 as a versatile tool for engineering biology. Nature methods 10, 957-963 (2013).
19. O. Shalem et al., Genome-scale CRISPR-Cas9 knockout screening in human cells. Science 343, 84-87 (2014).
20. T. Wang, J. J. Wei, D. M. Sabatini, E. S. Lander, Genetic screens in human cells using the CRISPR-Cas9 system. Science 343, 80-84 (2014).
21. Y. Zhou et al., High-throughput screening of a CRISPR/Cas9 library for functional genomics in human cells. Nature, (2014).
22. C. Kuscu, S. Arslan, R. Singh, J. Thorpe, M. Adli, Genome-wide analysis reveals characteristics of off-target sites bound by the Cas9 endonuclease. Nat Biotechnol 32, 677-683 (2014).
23. P. Mali et al., CAS9 transcriptional activators for target specificity screening and paired nickases for cooperative genome engineering. Nat Biotechnol 31, 833-838 (2013).
24. L. A. Gilbert et al., CRISPR-mediated modular RNA-guided regulation of transcription in eukaryotes. Cell 154, 442-451 (2013).
25. L. S. Qi et al., Repurposing CRISPR as an RNA-guided platform for sequencespecific control of gene expression. Cell 152, 1173-1183 (2013).
26. B. Chen et al., Dynamic imaging of genomic loci in living human cells by an optimized CRISPR/Cas system. Cell 155, 1479-1491 (2013).
27. A. W. Cheng et al., Multiplexed activation of endogenous genes by CRISPR-on, an RNA-guided transcriptional activator system. Cell research 23, 1163-1171 (2013).
28. F. Meitinger et al., 53BP1 and USP28 mediate p53 activation and G1 arrest after centrosome loss or extended mitotic duration. J Cell Biol 214, 155-166 (2016).
29. T. Wang et al., Identification and characterization of essential genes in the human genome. Science 350, 1096-1101 (2015).
30. T. Hart et al., High-Resolution CRISPR Screens Reveal Fitness Genes and Genotype-Specific Cancer Liabilities. Cell 163, 1515-1526 (2015).
31. J. G. Doench et al., Rational design of highly active sgRNAs for CRISPR-Cas9-mediated gene inactivation. Nat Biotechnol 32, 1262-1267 (2014).
32. J. G. Doench et al., Optimized sgRNA design to maximize activity and minimize off-target effects of CRISPR-Cas9. Nat Biotechnol, (2016).
33. R. Huang, P. Fang, B. K. Kay, Improvements to the Kunkel mutagenesis protocol for constructing primary and secondary phage-display libraries. Methods 58, 10-17 (2012).
34. T. A. Kunkel, Rapid and efficient site-specific mutagenesis without phenotypic selection. Proc Natl Acad Sci USA 82, 488-492 (1985).

The invention claimed is:

1. A method for generating a covalently closed circularized (ccc) DNA based small RNA expression vector or vector library, the method comprising the steps of:
   (a) providing a single stranded (ss) phagemid vector comprising (i) at least one small RNA expression cassette comprising a RNA promoter and an empty target-small-RNA-sequence-introduction-site or a small RNA coding sequence, or partial sequence thereof, (ii) at least one f1-origin for replication (ORI) of single strand DNA,
   (b) providing at least one species of mutagenic RNA or DNA-Primer, wherein the mutagenic RNA or DNA-primer has the following structure in 3' to 5' direction: a first homology region, a target sequence region encoding for a small RNA to be expressed, and a second homology region, wherein the first homology region is complementary to, or is capable of annealing to, a sequence of the ss-phagemid vector construct flanking the empty target-small-RNA-sequence-introduction-site or the small RNA or DNA coding sequence, or partial sequence thereof, on the 5' side, and wherein the second homology region is complementary to, or is capable of annealing to, a sequence of the ss-phagemid vector construct flanking the empty target-small-RNA-sequence-introduction-site or the small RNA coding sequence, or partial sequence thereof, on the 3' side,
   (c) annealing of at least one species of mutagenic RNA or DNA-primer to the ss-phagemid vector construct and amplifying a covalently closed circularized (ccc)-heteroduplex dsDNA therefrom, and
   (d) removing residual wild type phagemid vector DNA, wherein the small RNA is a siRNA, shRNA, an anti-miR, or a guide RNA (gRNA).

2. The method according to claim 1, wherein the small RNA is a gRNA, and wherein the ss-phagemid vector construct comprises further a RNA or DNA or genome editing nuclease expression sequence in wild type or engineered form, optionally operably linked to a stable promoter or an inducible promoter.

3. The method according to claim 1, wherein the at least one species of mutagenic DNA-primer is at least two species of mutagenic DNA-primer, and wherein each species of cccDNA has a different sequence in the small RNA coding sequence of choice.

4. The method according to claim 1, wherein a multitude of mutagenic DNA-primer species are provided by introducing into the small RNA coding sequence of choice at least one or more IUPAC-encoded bases.

5. The method according to claim 1, wherein small RNA coding sequence is at least 10 nucleotides to 200 nucleotides long.

6. The method according to claim 1, wherein each of the homology regions has a length of at least 5 nucleotides.

7. The method according to claim 1, wherein the muta-genic DNA-primer has a sequence according to any of SEQ ID NO: 1 to 12.

8. The method according to claim 1, the method comprising the steps of:
   (a) providing a single stranded (ss) phagemid vector construct comprising at least one uracil base; the ss-phagemid vector construct comprising (i) at least one small RNA expression cassette comprising a RNA promoter and an empty target-small-RNA-sequence-introduction-site or a small RNA or DNA coding sequence and/or a DNA or RNA nuclease target sequence, or partial sequence thereof, (ii) at least one fl-origin for replication (ORI) of single strand DNA,
   (b) providing at least one species of mutagenic DNA-Primer, wherein the muta-genic DNA-primer has the following structure in 3' to 5' direction: a first homology region, a target sequence region encoding for a small RNA to be expressed, and a second homology region, wherein the first homology region is complementary to, or is capable of annealing to, a sequence of the ss-phagemid vector construct flanking the empty target-small-RNA-sequence-introduction-site or the small RNA coding sequence, or partial sequence thereof, on the 5' side, and wherein the second homology region is complementary to, or is capable of annealing to, a sequence of the ss-phagemid vector construct flanking the empty target-small-RNA-sequence-introduction-site or the small RNA coding sequence, or partial sequence thereof, on the 3' side,
   (c) annealing of at least one species of mutagenic DNA-primer to the ss-phagemid vector construct and amplifying a covalently closed circularized (ccc)-heteroduplex dsDNA therefrom, and
   (d) replacing the uracil-containing strand in the ccc-heteroduplex dsDNA with a non-uracil containing complementary DNA strand to obtain a cccDNA based small RNA expression vector or vector library,
   wherein the small RNA is a siRNA, shRNA, an anti-miR, or a guide RNA (gRNA).

9. The method according to claim 8, wherein the single stranded (ss)-phagemid vector construct is provided by
   (aa) amplification of a dsDNA phagemid vector of the same sequence in a bacterial strain proficient or deficient for dUTPase and/or uracil glycosylase, and/or their homologs, paralogs or orthologues, to obtain wild type or uracil containing heteroduplex dsDNA phagemid vectors and
   (bb) generation of phage particles comprising a wild type or uracil containing ssDNA, and
   (cc) purifying from said phage particles said wild type or uracil containing ssDNA to obtain the ss-phagemid vector construct comprising at least one uracil base.

10. The method according to claim 9, wherein the bacterial strain deficient for dUTPase and/or uracil glycosylase, and/or their homologs, paralogs or orthologues, comprises a helper phagemid, or wherein in step (bb) said bacterial strain deficient for dUTPase and/or uracil glycosylase, and/or their homologs, paralogs or orthologues, is infected with a helper phage.

11. The method according to claim 8, wherein step (d) is performed by transforming and amplifying said ccc-heteroduplex dsDNA in a bacterium having a functional dUTPase and/or uracil glycosylase activity to obtain said cccDNA.

12. The method according to claim 1, wherein the amplification of a covalently closed circularized (ccc)-heteroduplex dsDNA in step (c) is performed by using an enzyme having RNA or DNA polymerase activity, optionally in conjunction with a RNA or DNA ligase.

13. A vector library obtainable by a method according to claim 1.

14. The method according to claim 9, wherein the bacterial strain proficient or deficient for dUTPase and/or uracil glycosylase, and/or their homologs, paralogs or orthologues is the CJ236 strain.

15. The method according to claim 11, wherein the bacterium having a functional dUTPase and/or uracil glycosylase activity is an electrocompetent *E. coli*.

16. The method according to claim 12, wherein the enzyme having RNA or DNA polymerase activity is a T7 DNA polymerase.

17. The method according to claim 12, wherein the RNA or DNA ligase is a T4 DNA ligase.

18. The method of claim 1, wherein the single stranded (ss) phagemid vector further comprises a DNA or RNA nuclease target sequence.

19. The method of claim 1, wherein the single stranded (ss) phagemid vector comprises deoxyuridine.

* * * * *